(12) United States Patent
Abbud-Antaki

(10) Patent No.: US 9,102,984 B2
(45) Date of Patent: Aug. 11, 2015

(54) SYSTEMS AND METHODS FOR INDIVIDUALIZED FUNCTIONAL GENOMIC PROFILING RELATED TO CANCER CELL GROWTH

(76) Inventor: Rula Abbud-Antaki, Allison Park, PA (US)

( * ) Notice: Subject to any disclaimer, the term of this patent is extended or adjusted under 35 U.S.C. 154(b) by 57 days.

(21) Appl. No.: 13/441,855

(22) Filed: Apr. 7, 2012

(65) Prior Publication Data

US 2012/0258885 A1    Oct. 11, 2012

Related U.S. Application Data

(60) Provisional application No. 61/473,222, filed on Apr. 8, 2011.

(51) Int. Cl.
| | |
|---|---|
| *C40B 30/06* | (2006.01) |
| *C12Q 1/68* | (2006.01) |
| *C12N 15/113* | (2010.01) |
| *G01N 33/50* | (2006.01) |
| *G01N 33/574* | (2006.01) |

(52) U.S. Cl.
CPC .......... *C12Q 1/6886* (2013.01); *G01N 33/5011* (2013.01); *C12N 15/113* (2013.01); *C12Q 2600/112* (2013.01); *C12Q 2600/178* (2013.01); *G01N 33/5088* (2013.01); *G01N 33/574* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2007/0010469 A1* | 1/2007 | Chan et al. ...................... | 514/44 |
| 2010/0028863 A1* | 2/2010 | Abbud-Antaki .................. | 435/6 |

* cited by examiner

*Primary Examiner* — Tracy Vivlemore
*Assistant Examiner* — Karen S Weiler
(74) *Attorney, Agent, or Firm* — Acker Wood IP Law, LLC; Gwen R. Acker Wood

(57) ABSTRACT

The present invention provides systems and methods for identification of genes related to cancer cell growth. In particular, the present invention provides functional genomic profiling of primary patient cells for identification of targeted and efficacious patient and cell-specific treatment modalities by employing a cancer biochip system (CBCS) which demonstrates improved plating efficiency, improved transfection efficiency and improved silencing efficiency. The present invention also provides a method of classifying a cancer patient based on response of cancer cells of the patient to a plurality of active agents for prediction of efficacious treatment of the cancer patient.

22 Claims, 16 Drawing Sheets

SYSTEMS AND METHODS FOR INDIVIDUALIZED FUNCTIONAL GENOMIC PROFILING RELATED TO CANCER CELL GROWTH

CROSS REFERENCE TO RELATED APPLICATIONS

The present application claims priority to U.S. Provisional Patent Application No. 61/473,222, filed Apr. 8, 2011, which is incorporated herein by reference in its entirety.

This invention was made with Government support under a Phase 1 SBIR Grant No. 1 R43 CA141962, awarded by the National Cancer Institute. The Government may have certain rights in the invention.

FIELD OF THE INVENTION

The present invention relates to systems and methods for identification of genes related to cancer cell growth and, in particular, to systems and methods for individualized identification and targeting of genes that affect cancer cell growth in a patient to optimize cancer diagnosis and therapy in the patient.

BACKGROUND OF THE INVENTION

Advances in genomic research have shown that each patient has their own unique tumor profile with patient-specific genetic variations. While silencing RNA (siRNA) screening tests can identify which genes drive tumor cell growth, results obtained from these assays have been limited in their clinical translatability because they employ cell lines growing on flat surfaces. Cell lines exhibit extensive chromosomal instability and behave differently depending on the culture conditions. Cellular response to siRNA in these assays is thus influenced by their attachment to the culture surface and cell-cell contact.

Anchorage-independent three-dimensional (3D) growth assays are considered to be the gold-standard for chemosensitivity testing, and leads identified with these assays have high probability of clinical success. These assays utilize different types of matrices, including soft agar, to inhibit cellular attachment and allow for 3D growth of cells. Transformed tumor cells and stem cells, but not normal cells, are capable of growing under these conditions, since they have the innate capability of uncontrollable cell division. For example, normal epithelial cells depend on cell-cell contact and attachment to a physical support for survival and growth.

In their current format, however, anchorage-independent growth assays are not amenable for large-scale screening because they require large numbers of cells and the plating efficiency of human tumor biopsies is very low. Furthermore, current assays are capable of testing only one inhibitor at a time and are tedious, time consuming, and costly since they are not easily amenable to automation.

Moreover, the current systems and methods known in the art for identifying, diagnosing and treating cancer cells are not capable of being used on an individual or a personalized basis for patient-specific therapy. There is a need, therefore, for an individualized or personalized large-scale screening assay system for identification of genes responsible for anchorage-independent cancer cell growth and for identification of cell-specific inhibitors of cancer cell growth to optimize cancer diagnosis and therapy.

SUMMARY OF THE INVENTION

The present invention provides a personalized diagnostic tool to classify tumor cells in a specific patient based on its functional genomic profile and personalized systems and methods for the identification and targeting of specific genes that affect cancer cell growth in a specific patient.

In one aspect, the present invention provides a method of classifying a cancer patient based on response of cancer cells of the patient to one or more of a plurality of active agents for prediction of efficacious treatment of the cancer patient. The method includes obtaining a tumor biopsy from a patient, isolating tumor cells from the tumor biopsy, detecting and identifying one or more abnormal genotypes in the tumor cells, obtaining a biochip comprised of at least one slide coated with a base layer comprising a first matrix and a plurality of spots, wherein the plurality of spots comprise a plurality of active agents capable of influencing tumor cell growth by affecting gene expression, adding a second matrix that is mixed with, or layered atop of, the tumor cells, wherein the tumor cells are exposed to and/or incorporate the plurality of active agents, and wherein the first matrix and the second matrix support anchorage-independent three-dimensional growth and the second matrix limits tumor cell migration, growing the tumor cells, measuring the growth of the tumor cells, and determining and identifying which one or more of the plurality of active agents affects the growth of the tumor cells of the patient in order to classify the patient's cancer.

In another aspect, the present invention provides a cancer biochip system (CBCS) for assaying cancer cells from a patient to classify the patient's cancer based on response of the cancer cells to one or more of a plurality of active agents for prediction of efficacious treatment of the cancer patient. The CBCS includes a cancer biochip comprising at least one slide coated with a base layer. The base layer is comprised of a first matrix and a plurality of spots. The plurality of spots comprises a plurality of active agents capable of influencing tumor cell growth by affecting gene expression. The first matrix prevents cell attachment and supports anchorage-independent cell growth. The cancer biochip also is comprised of a second matrix for mixing with, or for layering atop of, tumor cells isolated from a tumor biopsy of a patient. The tumor cells are plated on the first matrix and exposed to and/or incorporate the plurality of active agents. The second matrix allows the tumor cells to grow into discrete colonies, supports anchorage-independent three-dimensional cell growth and limits cell migration. The growth of the tumor cells of the patient are measured to determine and identify which one or more of the plurality of active agents affects the patient's tumor cell growth in order to classify the patient's cancer.

Suitable active agents include, without limitation, DNA, RNA, siRNA, shRNA, antibodies, small molecules, proteins, peptides, peptidomimetics, pharmaceutical compositions, drugs and combinations thereof.

In one embodiment, the one or more active agents include siRNA.

Each one of the plurality of active agents of the present invention may affect at least one gene and/or at least one expressed gene of the patient.

The at least one gene or at least one abnormally expressed gene which may be affected by the one or more active agents may include, without limitation, proliferation genes such as MK167, AURKA, BIRC5, CCNB1 and MYBL2; estrogen-related genes such as ESR1, PGR, BCL2, SCUBE2 and ESR2; HER2 genes such as ERBB2 and GRB7; invasion genes such as CTSL2, MMP11, CD68, BAG1 and GSTM1; druggable gene targets such as IGF1 R, TNFRSF10A, TNFRSF10B, FNTB, BRAF, MAPK1, PIK3CA, CSK, HSPCA, HDAC1, DNMT1 and DMAP1; and ACTB, GAPDH, RPLPO, GUSB, TFRC and cyclophilin.

In an embodiment, the first matrix and/or the second matrix includes at least one transfection agent. Suitable transfection agents include, without limitation, chemical transfection agents, lipid-based transfection agents, cationic lipid transfection agents, non-lipid based transfection agents, electroporation, molecular-based transfections, laser-mediated transfection, pinocytosis transfection, osmotic lysis transfection, microinjection, viral delivery systems and combinations thereof.

The tumor cells from a patient may include a detectable label such as selectable markers, fluorescent markers, fluorescent nanocrystals, quantum dots, fluorescent proteins, bacterial enzymes, or combinations thereof.

The thickness of the first matrix and/or the second matrix ranges between about 0.1 mm to about 1.0 mm thick and provides an environment in which cancer cells can grow into discrete colonies. Any of the following coatings or a combination of coatings may be used in the present invention: soft agar, agarose, hydrogels, methylcellulose alginate hydrogel, polyvinyl alcohol-hydrogel, collagen vitrigel, poly(2-hydroxylmethacrylate) hydrogels, PVP/PEO hydrogels or copolymers of 2-methacryloyloxyethyl phosphorylcholine. The matrix allows for the cells plated on the slide to form discrete colonies.

Each slide is able to hold from about 1 to about 150,000 spots that are about 65 to about 120 μm in diameter. Suitable slides of the present invention include, without limitation, chamber slides, glass slides, polymer slides, plastic slides, polystyrene slides, quartz wafers, or combinations thereof. In one embodiment, the slide is a calibration chip comprised of positive and negative control agents which optimize cancer cell culture modalities, specificity of active agents, transfection methods and reproducibility of the assay.

The plurality of active agents are separated from one another on the at least one slide by using at least one or a plurality of spots or wells formed within the slide, by using at least one or a plurality of spots or wells created by placing a removable member on the slide, wherein the removable member contains at least one or a plurality of orifices which act to separate each of the one or more active agents from each other, or by using at least one or a plurality of demarcations etched into the slide which serves to separate each one of the one or more active agents.

The methods and systems of the present invention include a means for observing tumor cells grown on the Cancer Biochip System (CBCS) such as, without limitation, microscopy, scanning, laser scanning, fluorescence detection, automated fluorescence detection, a CCD camera, cell counter, automated colony counter, the human eye, FACS or combinations thereof.

The present invention also includes the use of a computer program to identify and count colonies of living tumor cells in real-time by the CBCS.

BRIEF DESCRIPTION OF THE DRAWINGS

A fuller understanding of the nature and advantages of the present invention can be gained from the following description when read in conjunction with the accompanying drawings.

DETAILED DESCRIPTION OF THE INVENTION

The present invention provides personalized systems and methods for the identification and targeting of specific genes that affect cancer cell growth to optimize cancer diagnosis and therapy in a specific patient.

The present invention includes the CBCS as a personalized cancer diagnostic and therapeutic tool to classify tumors according to their functional genomic profile and to identify genes that are required for anchorage-independent tumor cell growth. The CBCS as a diagnostic tool in accordance with the present invention provides individualized, cell-based in vitro cancer diagnostic testing and selection of patient-specific optimal therapies. As a result, histological evaluation of tumor grade can be replaced by assays for tumor gene expression profiles, i.e., detection and identification of cancer-initiating genes, which genes then can be targeted for individualized therapy.

The CBCS of the present invention is described in U.S. Pat. Nos. 7,537,913 and 8,110,375, and U.S. patent application Ser. No. 13/292,221, which are incorporated herein by reference. U.S. Pat. No. 7,537,913 describes a kit for assaying cells, and U.S. Pat. No. 8,110,375 describes a method for identifying cancer causing genes using the CBCS.

The CBCS in accordance with the present invention can be used for real-time examination of cancer cell growth. For example, colony growth of cancer cells may be monitored up to one month during which time data are regularly collected. In cases of extremely aggressive cancer, significant growth can occur in as little as one day. The time needed for obtaining clinically relevant results from the diagnostic tool may range from about 7 to 21 days. This time period provides sufficient time to obtain highly definitive results.

The technological innovation provided by the CBCS includes high-throughput screening for inhibitors of anchorage-independent cancer cell growth through a fast one-step transfection approach of active agents with live monitoring and quantification of colony cell growth. By miniaturizing the assay conditions, the need for large quantities of tumor cells and reagents are eliminated, thereby significantly lowering the cost.

In an embodiment, the present invention includes silencing RNA (siRNA)-based cancer target identification and validation, cell-based in vitro diagnostics, and personalized therapeutics. The assay system of the present invention allows this functionality data to be obtained more quickly than in other approaches and with a higher level of predictability of in vivo results. In accordance with this embodiment, a high-density CBCS may be used for large-scale cancer target identification and validation. This is achieved by testing primary patient samples on the CBCS, and then classifying tumors based on their responsiveness to suppression of abnormally expressed genes by siRNA.

Figure 1:
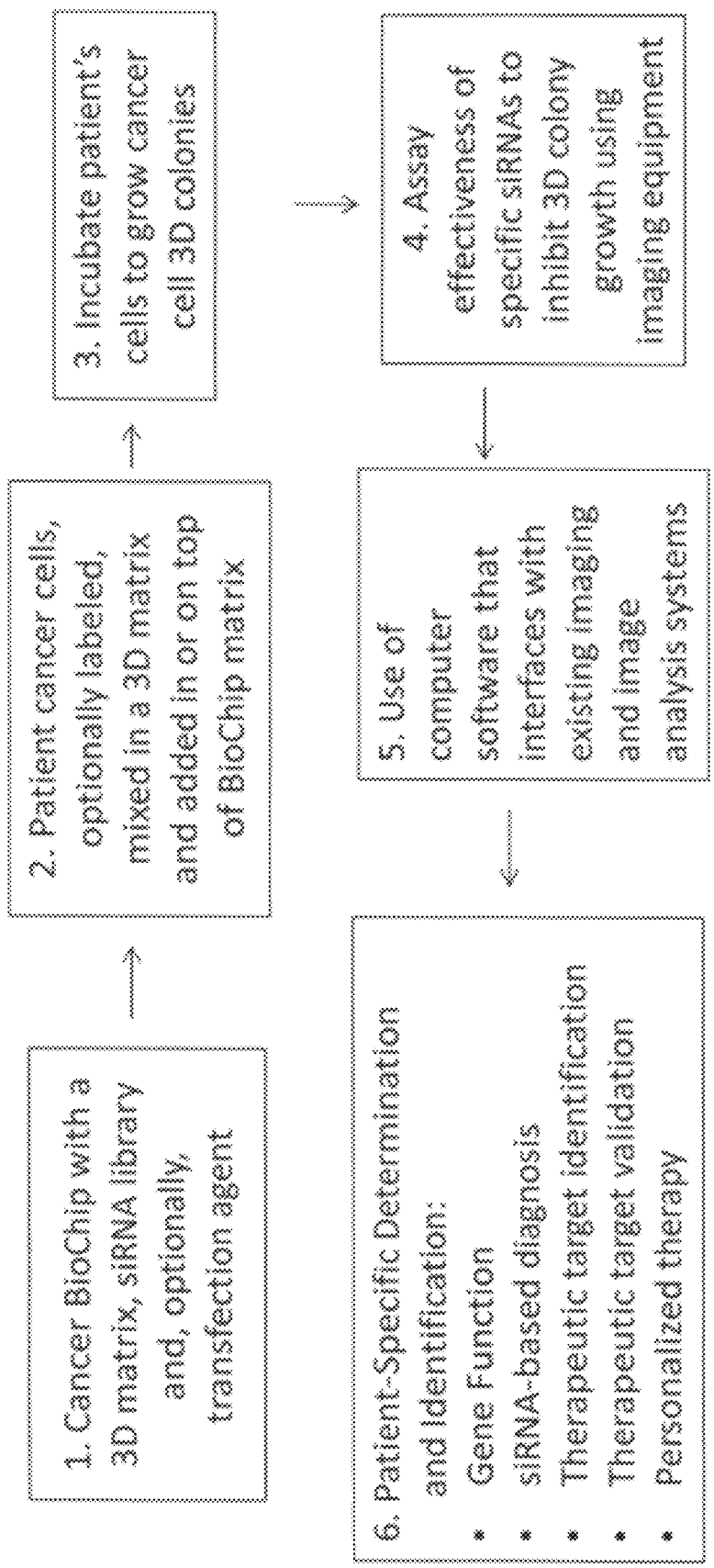
FIG. 1 is a flow chart of the CBCS system and method according to the embodiments of the present invention.

The CBCS of the present invention includes a proprietary biochip (referred to as a "Test Cancer BioChip" or "Cancer BioChip") and a matrix that inhibits attachment of cells to the slide and supports anchorage-independent growth, which is designed to interface with a variety of commercially available microarray robots and imaging systems. In one embodiment, as shown in FIG. 1, the Cancer BioChip contains siRNA embedded in a 3D first matrix (1). Cancer cells from a patient are mixed with a second 3D matrix and applied in or on top of the first matrix (2). Transformed tumor cells selectively grow in an anchorage-independent fashion, forming colonies that incorporate the underlying siRNA (3). The effectiveness of specific siRNAs to inhibit colony growth then is assayed using custom microscopic imaging equipment (4). Computer software is used to interface with existing imaging and image analysis systems (5). The end result is the determination and identification in a specific patient of the following: gene function, siRNA-based diagnosis, therapeutic target identification, therapeutic target validation, and personalized therapy (6).

The CBCS of the present invention allows for determination of the role of abnormal genes and/or abnormally expressed genes in cancer cell growth of a specific patient. Genes detected and identified that are essential for anchorage-independent cancer cell growth in a specific patient in accordance with the present invention will be deemed potential therapeutic targets for the patient. Although many genes are expressed abnormally in cancer cells, only a few are involved in the initiation and maintenance of the abnormal cell growth associated with cancer. Thus, using the CBCS, individualized silencing of tumor genes provides a more refined level of tumor classification and information about potential siRNA and non-siRNA-based therapeutics.

The CBCS can be used for any type of cancer. In one embodiment, primary breast cancer cells are grown on a first-generation Cancer BioChip (referred to as "CBC-1") consisting of 50 wells, with each well containing a base layer of agar, a middle layer of siRNA in agar, and a top layer of cells in agar. These cells incorporate underlying siRNA at high efficiency and show siRNA-mediated suppression of target genes. Because growth conditions vary between different cells, the CBCS in accordance with the present invention has been developed to optimize plating, transfection, silencing and cytostatic efficiencies, and the CBC-1 may be used to optimize conditions prior to application of patient cells on the high-throughput CBCS. The CBCS also enables the development and provision of a target-validation screening service.

Currently, patients with cancer, such as breast cancer, are diagnosed based on the expression of a very limited number of genes. Novel gene expression-based prognostic tests, such as the Oncotype Dx or MammaPrint assays rely only on 21 or 70 genes, respectively. However, basic studies of gene expression signatures have revealed that breast cancer is a much more heterogeneous disease, which explains the variability in clinical outcome from seemingly identical patients. Currently, published research in molecular classification of breast cancer has identified 476 genes which segregate breast cancer patients into five subtypes: Luminal-A, Luminal B, Basal-like, Normal-like and Her-2. Other gene signatures also have identified: claudin-low, apocrine and interferon subtypes. The CBCS in accordance with the present invention allows for the identification of which of the abnormally expressed tumor genes are responsible for anchorage-independent tumor growth. It is envisioned that the entire human genome may be included on the CBCS.

A particular advantage of the CBCS of the present invention is its specificity, which distinguishes it from Oncotype Dx or MammaPrint assays. Currently, patients with "high recurrence scores" on these assays have very little recourse since it is not possible to determine which of the 21 or 70 genes need to be targeted for therapy. By identifying the specific genes that drive tumor growth in a patient, the CBCS is able to guide the clinician to select the appropriate drug from those currently available.

Although studying the expression pattern of cancer "signature" genes could be assumed to improve accuracy of classifying and staging of cancer patients, as well as determining the choice of existing chemotherapies, data are not yet available on which genes need to be targeted for treatment. Targeting a small number of genes may not be sufficient to eliminate all malignant cells, especially since these gene lists show very little overlap, and the targeting of some genes may have detrimental effects on healthy cells. Thus, using the CBCS in accordance with the present invention enables clinicians in an in vitro setting to understand the role of these genes in tumor initiation and progression and to then develop efficient and targeted therapies for cancer, such as, but not limited to, breast cancer.

Functional screening of candidate drug targets requires the development of gene-specific reporter systems and inhibitors. Double stranded RNA (dsRNA) can cause post-transcriptional gene silencing via RNA interference (RNAi) in most eukaryotic cells and, therefore, this is a desired approach for inhibiting gene expression. Silencing RNA includes dsRNA that is homologous to the gene of interest and inhibits post-transcriptional gene expression. When first introduced into the cell, it interacts with PIWI-family proteins to form the RNA-induced silencing complex (RISC), which recognizes and then degrades homologous mRNA.

The synthesis of siRNA can be accomplished chemically, by enzymatic digestion, or via RNA polymerase-mediated synthesis. Chemically synthesized siRNA can be further modified to achieve high delivery into target cells. Accell siRNA, commercially available from ThermoFisher Dharmacon, is a backbone modified siRNA, for efficient uptake by cells without the need for a transfection reagent. Stable expression of siRNA, however, requires use of expression cassettes for short hairpin RNA (shRNA) cloned in plasmid, retroviral, or lentiviral expression vectors. Short hairpin RNA libraries targeting a large number of human genes are now commercially available. Silencing RNAs have been shown to regulate critical developmental pathways during normal embryogenesis and have great therapeutic potential for the synthesis of gene-specific inhibitors for any candidate gene based on sequence. As a result, it is now possible to perform genome-scale gene silencing experiments for functional genomics and drug discovery. In a preferred embodiment, the CBCS of the present invention utilizes the above-described available siRNA libraries to provide a high-throughput, scalable siRNA platform as a tool for personalized cancer patient diagnosis and prognosis.

Preclinical studies have shown success of siRNA-based approaches for suppression of tumor growth in animal models. For cancer therapy, this approach is able to identify critical subsets of gene targets, since targeting one gene at a time may not be sufficient. The identification of legitimate targets for treatment of cancer requires the development of high-throughput cell-based siRNA screening assays. Several studies have been reported using genome-wide loss-of-function screens for the identification and validation of cancer drug targets. These studies have used either Transfected Cell Microarrays (TCM) or pooled shRNA libraries for the identification of shRNAs capable of altering function in cancer cell lines. Various transfection agents have been tested on cell-based microarrays. However, high-efficiency transfection of siRNA expressing vectors with long-term gene suppression in a broad range of cell types remains limited to viral delivery systems. Recently, lentivirus-infected cell microarrays (LICM) have been developed and may be used to obtain siRNA expression in immortalized and primary cells. This approach requires high-titer virus, whereby precautions are necessary in terms of biological safety.

While these studies support the feasibility of high-throughput gene silencing and the influence of gene expression on various parameters of cell function, none of these studies evaluates the functional impact of siRNA on cancer cell growth in a setting that would directly translate to the in vivo milieu. These assays have been developed to treat only attached cancer cell lines which have altered properties and biological responses that may not mimic in vivo cancer cell biology. Cells behave differently when grown in a three-dimensional matrix compared to flat, two-dimensional surfaces. Furthermore, cancer cells grown under these conditions tend to migrate, which limits the throughput capability of this assay, since individual siRNAs are spotted at distances that would keep neighboring cells apart. Another limitation is that it is not possible to study patient tumor cells with these assays since they allow both normal and tumor cell growth. Because cellular sensitivity to treatment is influenced by in vitro growth conditions, none of these assays can be used as a stand-alone cancer drug screening assay. Thus, it is important to perform these studies in an in vitro three-dimensional setting that could translate to the clinic.

Anchorage-independent growth assays also are known as soft agar, clonogenicity, human tumor colony-forming, or human tumor stem cell assay (HTSC). Anchorage-independent growth usually is quantified using semi-solid media, such as agar. Soft agar assays typically are the most stringent assays for cancer drug screening, since they allow transformed cells, but not normal cells, to grow in vitro. These transformed cells exhibit stem cell-like properties, grow in suspension, and exhibit minimal contact-triggered growth inhibition.

There is a clear correlation between in vitro results obtained using an HTSC assay and the clinical responses of myeloma and ovarian cancer patients to a variety of chemotherapeutic agents. Larger-scale testing has revealed that clinically effective chemotherapeutic agents also are active in the HTSC assay with the exception of those requiring systemic activation. Clinically ineffective agents have been confirmed to be true negatives with 97% accuracy. "Clonogenic" assays are used as secondary screens for cancer patients. The commercially available Oncotech Extreme Drug Resistance (EDR) assay, which predicts the failure of chemotherapy prior to patient treatment, is one representative example of a clonogenic assay.

Table 1 shows the features of the CBCS as compared to other technologies, such as DNA microarrays/gene chips, transfected cell microarrays and regular anchorage-independent growth assays.

TABLE 1

Comparison between CBCS and Other Technologies

| Method | High-throughput | Functional Data | Automated | Highly predictive of in vivo results | Test siRNA for entire genome | Real-time monitoring of colony growth | Tests for resistance | Minimizes use of reagents | Labor and time savings |
|---|---|---|---|---|---|---|---|---|---|
| CBCS | Yes | Yes | Yes | Yes | Yes | Yes | Yes | Yes | Yes |
| DNA microarrays/gene chips | Yes | No | Yes | No | No | N/A | No | Yes | Yes |
| Transfected cell microarrays | Some | Yes | Yes | No | Some | Some | No | No | Yes |
| Anchorage-independent growth assays | No | Yes | No | Yes | No | No | No | No | No |

As Table 1 shows, the extraordinary advantage of the CBCS of the present invention compared to these other technologies is that it demonstrates all of the following properties: high-throughput, automated, highly predictive of in vivo results, tests siRNA for the entire genome, allows for real-time monitoring of cancer cell growth, tests for resistance, minimizes use of reagents and cells, and is labor and time saving.

EXAMPLES

The present invention is more particularly described in the following non-limiting examples, which are intended to be illustrative only, as numerous modifications and variations therein will be apparent to those skilled in the art.

Example 1

CBCS Validation Studies for Patient-Specific Functional Genomic Profiling

This investigation was undertaken to provide validation of a first-generation CBCS, referred to as CBC-1, capable of simultaneous quantitative real-time assessment of the effect of 50 different siRNA mixtures on anchorage-independent tumor cell growth. Matrices employed in the CBC-1 consisted of soft agar. Cells plated on the CBC-1 incorporate the underlying siRNA and form colonies that can be examined and quantified over a long period of time. The CBC-1 therefore can be used to optimize basic functions of the CBCS prior to scaling tip to a high-throughput full genome screen. These include plating, transfection, silencing, and cytostatic efficiencies. This investigation reports on each of these parameters for the validation of the CBC-1 as a stand-alone in vitro test for identification of inhibitors of patient-specific breast cancer cell growth in a clinically relevant setting.

Materials and Methods
Silencing RNA

Accell ESR1 siRNA (ThermoFisher Dharmacon, LaFayette, Colo.) or Mission TRC shRNA expressing lentiviral vectors (Sigma, Saint Louis, Mo.) were used. Accell siRNA controls included Accell Non-targeting and Accell Green Non-targeting siRNA. The Mission TRC shRNA expressing lentiviral vectors were: Mission pLKO.1-puro Control Transduction Particles, Mission TurboGFP Control Transduction Particles, and Mission eGFP shRNA Control Transduction Particles. Lentiviral vectors at a titre of $10^6$ particles/ml, providing 5000 particles per well, were mixed with Protamine Sulfate (6 μg/ml) and agar prior to application on the CBC-1.

Preparation of the CBC-1

A CBC-1 (Falcon Genomics, Inc., Pittsburgh, Pa.) that consisted of CultureWell chambered coverslips (Grace Biolabs, Inc., Bend, Oreg.), with each spot being about 3 mm in diameter and about 1 mm deep was used. After application of a base agar layer in each well, siRNA mixed with agar was applied, followed by cancer cells mixed with top agar. The CBC-1 was incubated in a $CO_2$ incubator at 37° C. overnight, covered with complete growth medium on the following day, and fed twice a week thereafter. Colony formation was monitored using an inverted microscope at different time intervals up to 20 to 29 days. At the end of the incubation period, cell viability was determined using MTT (3-(4,5-dimethylthiazol-2-yl)-2,5-diphenyltetrazolium bromide) stain.

Patient Cell Culture

Primary breast cancer cells from patients diagnosed with invasive breast cancer were procured from a commercial supplier (Celprogen, San Pedro, CA) or prepared in-house from fresh patient tumor tissue collected by the Cooperative Human Tissue Network (CHTN) funded by the National Cancer Institute, NIH. All patient tissues were procured by CHTN according to current regulations and guidance for repositories from the Office of Human Research Protections (OHRP, DHHS). Patient tumor samples were shipped from CHTN affiliated institutions in RPMI-1640 containing antibiotics, 10% Fetal Calf Serum, and 2.5 μg/ml Fungizone and maintained cold during shipment. Upon arrival, tissue was immediately processed for preparation of tumor cells. Collagenase types 3 and 1 (246 units/ml for 3-4 hours) (Worthington, Lakewood, NJ) were used sequentially to digest the tissue and to isolate the cells. This was followed by filtration through 40 μm Nylon cell strainers. The cells then were cultured in flasks coated with Geltrex (Invitrogen) in the presence of HuMEC medium (Invitrogen).

Cell Lines

Breast cancer cell lines, including MDA-MB-231, M4A4, MCF7, SKBR3, and immortalized fibroblast cells NIH-3T3 were obtained from the American Type Culture Collection (ATCC, Manassas, Va.). All cells were cultured according to ATCC guidelines in DMEM medium (Hyclone Laboratories, South Logan, Utah) for MCF7, NIH-3T3 and M4A4 cells, RPMI (Sigma) for SKBR3 cells, and Leibovitz's L-15 Medium (Sigma) for MDA-MB-231 cells, containing 10% Fetal Bovine Serum, 1% Antibiotics-Antimycotics (Invitrogen, Carlsbad, Calif.; Catalogue No. 15240-062) at 37° C. in the presence of 5% $CO_2$. Cells were passaged using Trypsin-EDTA (0.05%; Hyclone) when they reached 70-80% confluency in culture.

Imaging and Image Analysis

Individual wells were imaged on an inverted Motic AE31 microscope using high-resolution cooled CCD cameras; CoolSnap K4 (Photometrics, Inc.), or QiCam (Qimaging®). Several images were acquired along the z-axis and were processed to create z-stacks, which were subsequently merged using ImageJ (NIH).

Image analysis was performed using custom-designed image analysis macros in ImageJ. These macros measure number of cells/colonies, their average size, and the total area occupied by cells for each condition in an automated fashion. Change in average size from day 2 to later days is calculated and expressed as percent of controls. Relative change in colony number also was calculated by subtracting the number of colonies between day 2 and later time points, normalized to total cell counts at day 2, and expressed as a percent of controls. Growth curves were obtained by plotting the total area at different time points. Plating efficiency was determined by calculating the number of live colonies as a percent of total measured cells at day 2. Determination of both transfection and silencing efficiencies requires measurement of the presence or absence of a fluorescence signal in each cell or colony. Because cells grow in a three-dimensional matrix on the CBC-1, imaging of each cell and identification of its level of fluorescence signal requires acquisition of z-stacks in both bright field and fluorescence, respectively. For fluorescent signal analysis, Z-stacks first were merged using maximum intensity for the fluorescence images and minimum intensity for the bright field images. Background signal was subtracted from the merged fluorescence images. Particles ranging between 300 and 10,000 $\mu m^2$ were identified as Regions of Interest (ROI) in the merged bright field images. ROIs then were overlaid on the merged fluorescence image followed by measurement of the fluorescence intensity.

To determine transfection efficiency, background intensity of the fluorescence signal was calculated by averaging the maximum signal per colony from all colonies observed in the control wells (n=5 wells per experiment). Cells that expressed a signal intensity equivalent to the average background signal plus two times its standard deviation (average background signal +2*SD) were considered to be transfected by either Accell Green or Mission TurboGFP. Percent transfection efficiency was determined by dividing the number of transfected colonies by total number of cells observed in each well and multiplying by one hundred.

For silencing efficiency, the average integrated fluorescent signal density for all M4A4 colonies was measured in the presence or absence of Accell EGFP siRNA or Mission TRC EGFP shRNA. Data was expressed as percent EGFP signal relative to control.

Statistical Analysis

For plating efficiency experiments, a linear regression analysis was performed to determine the percent colonies formed at different starting concentrations of cells on the CBC-1. The slope of the linear regression determined plating efficiency. ANOVA followed by Student's t-test were used to compare between different experimental conditions.

Results

Anchorage-independent Growth of Breast Cancer Patient Cells and Cell Lines on the CBC-1 (Plating Efficiency)

High-throughput anchorage-independent growth testing is a unique property of the CBCS. Using the CBC-1, colony growth in agar of transformed breast cancer cell lines (MDA-MB-231, M4A4, MCF7, and SKBR3) and immortalized NIH-3T3 fibroblast cells was determined. Colony formation in all cells, but not in non-transformed NIH-3T3 cells, was observed. Plating efficiencies, as determined by percent of cells that formed live colonies, were between 20-39% for all of these cell lines.

Figure 2:
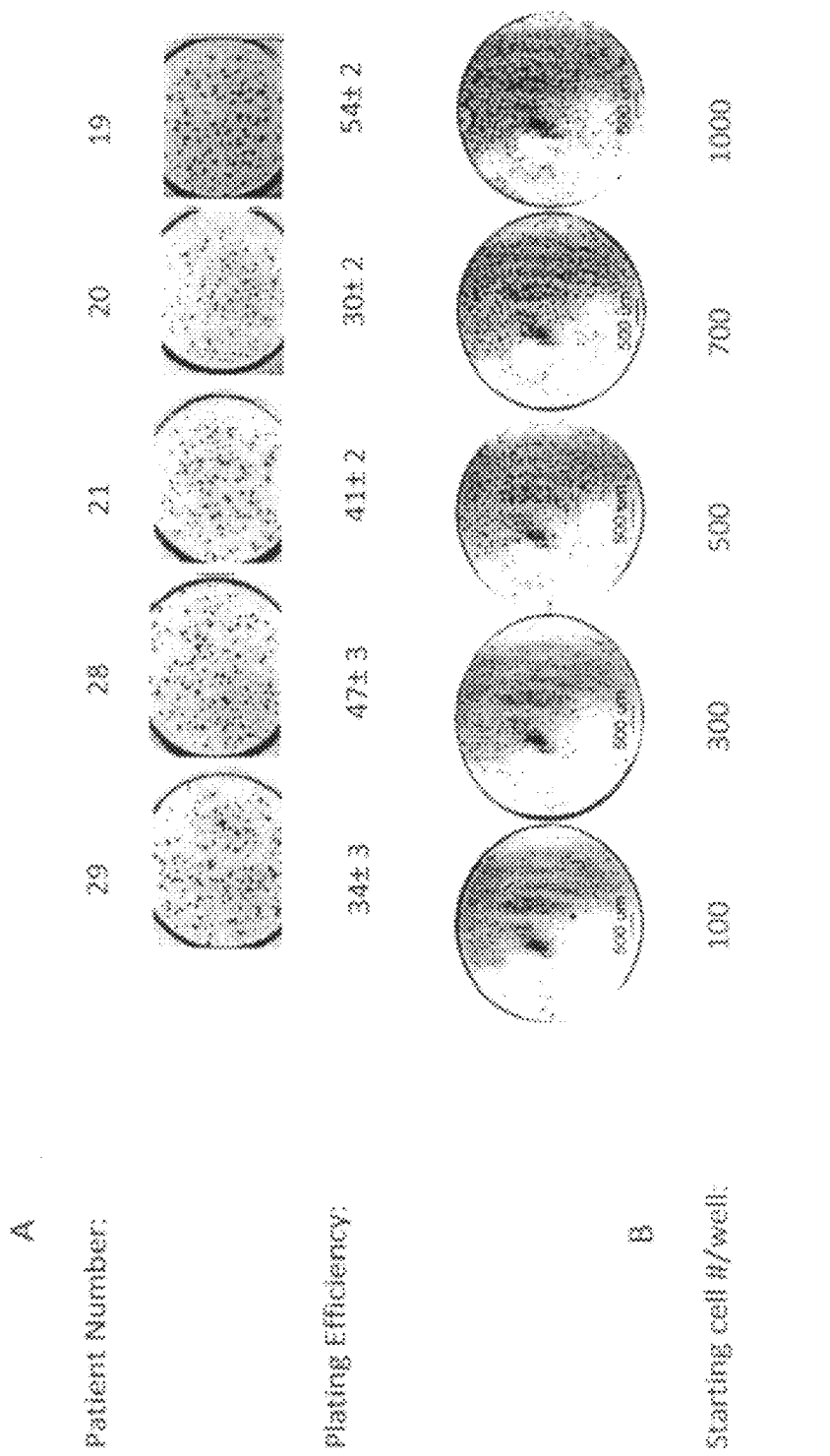
FIG. 2 shows plating efficiency of primary breast cancer patient cells on the CBC-1 according to the embodiments of the present invention. (A) are photomicrographs of MTT-stained CBC-1 imaged at days 21 to 22 (patients 19, 20, and 21) and days 28 to 29 (patients 28 and 29) in culture. (B) are bright field photomicrographs of growth of primary breast cancer patient cells on the CBC-1 after 9 days in culture, showing entire wells of the CBC-1 with 100, 300, 500, 700, and 1000 starting cell numbers/well. Colonies appear as black dots. (C) is a scatterplot showing the linear relationship between starting cell numbers and number of colonies forming in each well for the patient shown in (B).
Figure 2:
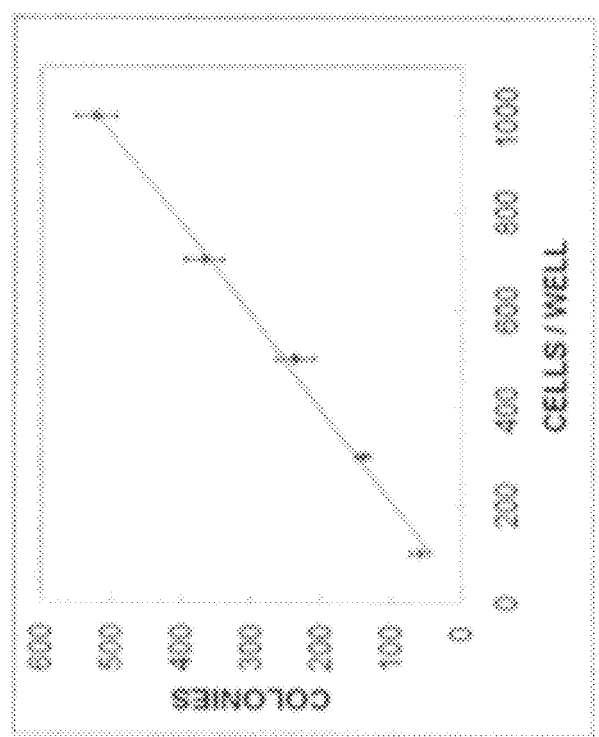

Analysis of colony formation on the CBC-1 for primary breast cancer cells from patients gave a wide range of results. Because these cells consisted of a mixture of all cell types obtained from a tumor, the percent of transformed tumor cells varied among patients. In addition, the growth rate of cells obtained from different patients was different. FIG. 2A shows examples of colonies that formed from 5 different breast cancer patients, and corresponding plating efficiencies.

For each patient, a plating efficiency experiment needs to be performed to identify the optimal starting cell number for each CBC-1. The number of colonies formed needs to be directly related to the starting cell counts. For these experiments, the plating efficiency was determined by measuring the percentage of colonies formed, after seeding 100, 300, 500, 700, and 1000 cells per well on the CBC-1 (n=5). FIGS. 2B and 2C show results from one representative experiment using primary breast cancer cells. FIG. 2B shows representative merged z-stack images from individual wells. Analysis of cell and colony size showed that the average cell area at day 1 was estimated to be 203±12 $\mu m^2$ and average colony size on day 9 was 1504±40 $\mu m^2$. For this patient, we have observed a linear correlation between starting cell numbers and numbers of formed colonies at day 9 (FIG. 2C) with an average plating efficiency of 51.6±2.5%. Thus, a starting cell number of 700 cells per well could be used for further testing on the CBC-1, whereby the assay would be in the linear range. These results show that the CBC-1 can be used to determine the plating efficiency of primary patient cells prior to functional genomic testing on a higher throughput CBCS.

Silencing RNA Transfection on the CBC-1 Using a Proprietary One-Step Method

The CBCS is intended to achieve efficient delivery of silencing RNA into primary cancer cells. Because different cells have different transfection efficiencies, it is essential to determine the method of choice for transfection for every cell type to be tested on the CBCS. This can be quickly achieved using the CBC-1. Silencing RNA can be delivered into cells cultured on the CBC-1 using different types of transfection reagents. Lentiviral-vector mediated delivery was tested using control vectors from the Mission TRC (Sigma) and Accell siRNA delivery methods (Dharmacon). The Accell siRNA method is unique, since it uses a proprietary siRNA backbone modification to drive uptake of the siRNA into the cells. As a result, there is no need for a separate delivery reagent. Another advantage of using Accell siRNA for use in the CBCS is that it does not require specialized equipment usually needed for safe manipulation of lentiviruses (Biological Safety Level 2+).

To determine transfection efficiency on the CBC-1 using either transfection method, the following positive controls were employed: the Mission TRC control vector, a lentiviral vector expressing the gene for Turbo Green Fluorescence Protein (TurboGFP), and the Accell Green siRNA control, a FAM-labeled Accell non-targeting siRNA. The impact of several variables was tested on expression of the Mission TRC TurboGFP control into primary patient cells and the MDA-MB231 breast cancer cell line. The TurboGFP signal in these cells was found to be very weak using Mission TRC TurboGFP. In both MDA-MB-231 and primary breast cancer cells, the transfection efficiency on the CBC-1 using the Mission TRC TurboGFP vector ranged between 8% and 20% (data not shown).

Figure 3:
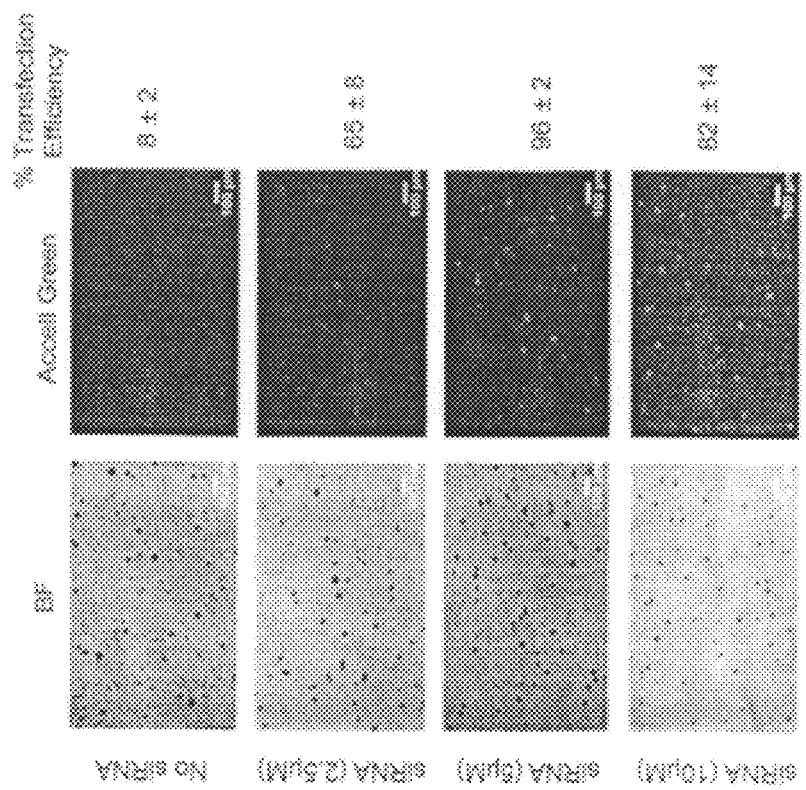
FIG. 3 provides representative photomicrographs showing expression of Accell Green in primary breast cancer cells according to the embodiments of the present invention. Shown are merged z-stacks for bright field (BF) and fluorescence (Accell Green) images. Treatment groups include no siRNA and Accell Green siRNA (2.5 uM, 5 uM, and 10 uM). Fluorescence Accell Green signal appears as gray areas.

In contrast, control Accell Green non-targeting RNAs gave a very strong signal in most primary breast cancer cells tested on the CBC-1. FIG. 3 shows representative photomicrographs of primary breast cancer cells growing on the CBC-1 in the presence of increasing doses of Accell Green (2.5 µM, 5 µM, and 10 µM). As shown in Table 2, while up to 65% transfection efficiency could be obtained at 2.5 µM Accell Green (65±8%), the highest transfection efficiency was observed at 5 µM (96±2%). No further increase in percent-transfected cells could be observed with the higher concentrations, and expression could be maintained at a lower level for up to 21 days. At day 21, colonies remained viable as

TABLE 2

Percent Transfection Efficiency of Accell Green into Primary Breast Cancer Cells at 5, 12, and 21 days post-transfection

| Accell Green | Day 5 | Day 12 | Day 21 |
|---|---|---|---|
| 0.0 µM | 8 ± 2 | 13 ± 5 | 5 ± 3 |
| 2.5 µM | 65 ± 8$^a$ | 50 ± 12$^a$ | 34 ± 3$^a$ |
| 5.0 µM | 96 ± 2$^{a,b}$ | 904 ± 2$^{a,b}$ | 66 ± 7$^{a,b}$ |
| 10.0 µM | 82 ± 14$^a$ | 72 ± 17$^a$ | 55 ± 14$^a$ |

$^a$p < 0.05 relative to 0.0 µM;
$^b$p < 0.05 relative to 2.5 µM, using Student's t-test.

determined by MTT stain (data not shown). However, the signal was not transmitted to all daughter cells in the colonies. Further testing of primary patient breast cancer cells (n=14) with Accell Green (10 µM) gave transfection efficiencies ranging between 55-95% at day 2 (data not shown). In summary, elevated siRNA expression was observed in primary breast cancer cells and cell lines on the CBC-1 using the Accell delivery method, while Mission TRC TurboGFP expression was much weaker.

Silencing Efficiency of EGFP siRNA in M4A4 EGFP-expressing Cells Growing on the CBC-1

Figure 4:
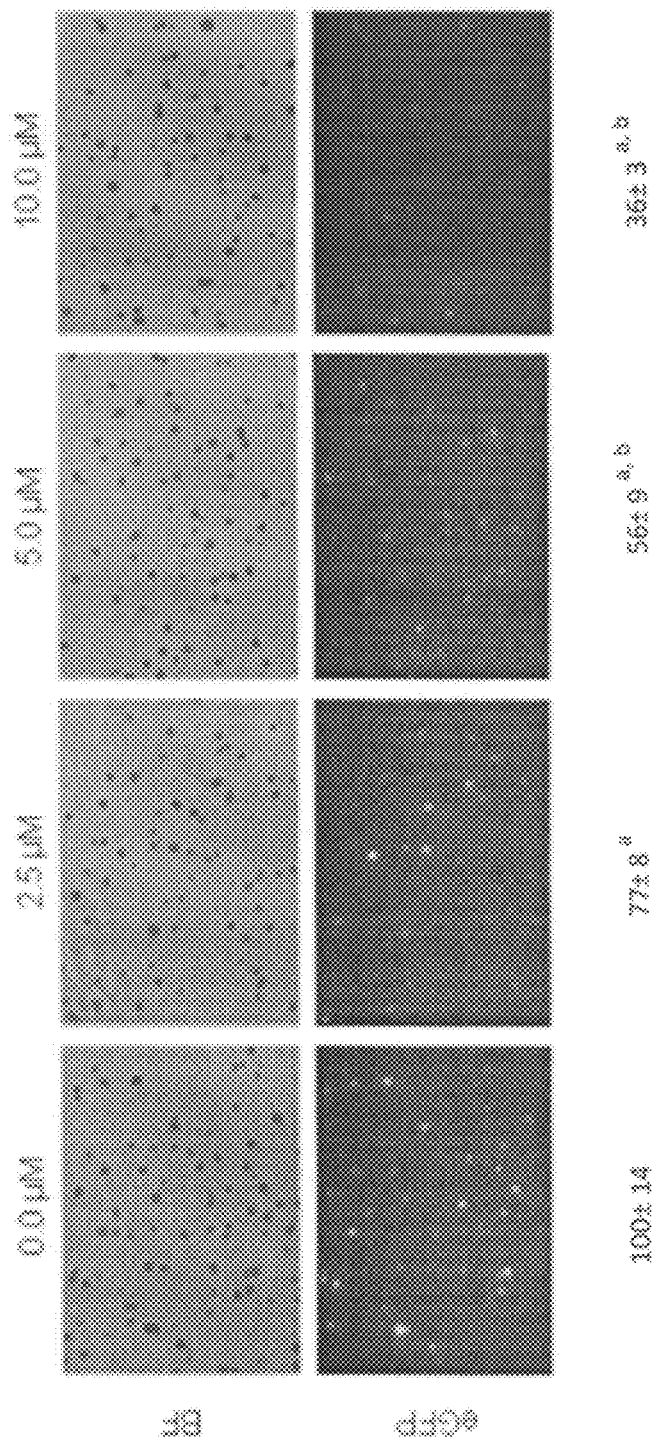
FIG. 4 provides photomicrographs which show suppression of EGFP signal in M4A4 breast cancer cells transfected with Accell EGFP pool siRNA on the CBC-1 after 8 days in culture according to the embodiments of the present invention. Photomicrographs show merged bright field (BF) z-stacks and merged green fluorescence z-stacks (EGFP). EGFP signal was expressed relative to controls (n=5); $^{a}P<0.05$ relative to control, and $^{b}P<0.05$ relative to 2.5 μM.

Successful transfection does not necessarily imply successful suppression of the gene of interest. The following experiments were performed to determine whether inhibition of gene expression on the CBC-1 could be achieved. Whether EGFP siRNA can suppress EGFP protein expression in breast cancer cell lines that have been engineered to express EGFP (M4A4 cells, ATCC) previously has been tested. Although high transfection efficiencies with the Mission TRC TurboGFP particles on the CBC-1 were not observed, gene silencing with both lentiviral transfection of shRNA for eGFP (Mission TRC control, Sigma; data not shown) and the Accell EGFP shRNA pool (ThermoFisher Dharmacon) was observed. FIG. 4 shows silencing of EGFP in M4A4 cells grown on the CBC-1 and transfected with increasing concentrations of Accell EGFP siRNA (2.5 µM, 5 µM, and 10 µM). Signal intensity for each colony was assessed by measuring average integrated density for all colonies. While maximal suppression of EGFP signal was 64% at day 8 with the Accell EGFP siRNA, it reached 93% with the Mission TRC EGFP shRNA at day 14 (data not shown).

These results prove that silencing of gene expression can be obtained even with low levels of lentiviral shRNA transfection efficiency. The most important deliverable in this CBC-1 assay is silencing of gene expression, which is obtained with either lentiviral vectors or Accell siRNA.

Suppression of MCF7 Colony Formation with Estrogen Receptor a (ESR1) siRNA on CBC-1

Figure 5:
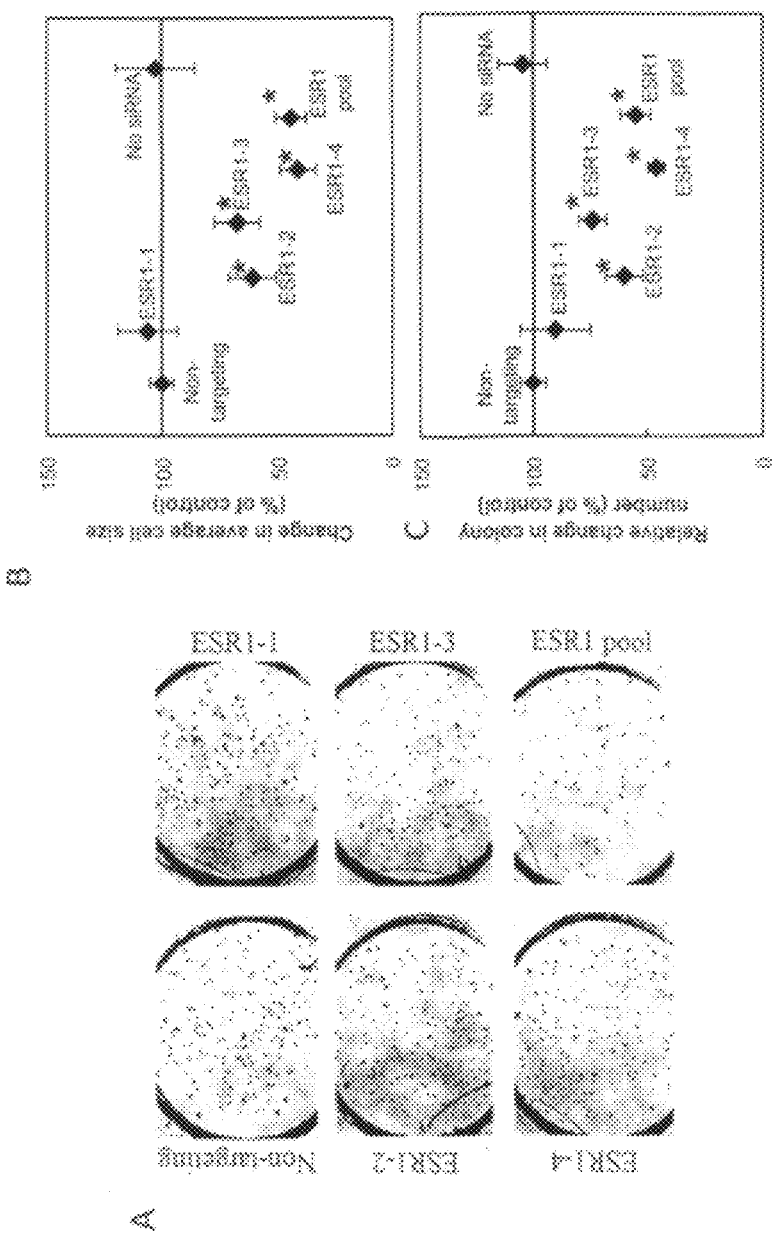
FIG. 5 shows suppression of MCF7 cell growth on the CBC-1 with Accell ESR1 siRNA according to the embodiments of the present invention. (A) are photomicrographs of merged z-stack images from different wells on the CBC-1 at day 7. Four different Accell siRNA sequences (ESR1-1, ESR1-2, ESR1-3, and ESR1-4) and a pool of all four were tested at 10 μM. Accell non-targeting was used as a negative control. Cells/colonies appear as dark dots. (B) shows changes in average MCF7 cell size, and (C) shows relative change in colony number between days 2 to 7 normalized to control (n=5). * indicates conditions that are significantly different from control (p<0.05).

The ultimate validation for the CBCS is the inhibition of cancer cell growth by siRNA knockdown of tumor genes. For these studies, we determined MCF7 breast cancer cell line growth response to ESR1 Accell siRNA on the CBC-1. MCF7 cells have been very well characterized and are known for their dependence on the estrogen receptor. For these experiments, four different Accell siRNAs (10 µM) targeting different sequences in the ESR1 gene were tested on the CBC-1 either individually (ESR1-1, ESR1-2, ESR1-3, ESR1-4) or together in a pool (ESR1 pool). In addition, each CBC-1 included the following controls: no cells, no siRNA, and Accell non-targeting siRNA (10 µM). FIG. 5A shows representative merged z-stack images from MCF7 cells after 7 days of culture on the CBC-1 in the presence of each of the above-described conditions. The number of colonies (size greater than 1,500 µm$^2$) as well as the average size of all cells was measured at different time points in culture. Measurement of relative change in colony numbers and change in average cell size from days 2 to 7 showed that ESR1-2, ESR1-3, ESR1-4 and ESR1 pools suppressed colony formation on the CBC-1 (FIGS. 5B and 5C), while ESR1-1 was ineffective. While untransfected cells (no siRNA) and cells transfected with non-targeting siRNA showed increase in number of colonies and average cell size over time, those transfected with ESR1 Accell siRNAs were suppressed except for ESR1-1. The highest level of colony suppression was obtained with either ESR1-4 or ESR1 pools. These results show that suppression of breast cancer colony growth on the CBC-1 can be achieved using siRNAs for genes known to be involved in breast cancer.

Discussion

The CBCS is a functional genomic assay which identifies inhibitors of anchorage-independent 3D cell growth. The studies presented herein show the efficacy of a first-generation Cancer BioChip, CBC-1, for initial determination of plating, transfection, silencing and cytotoxic efficiencies for every cell type prior to high-throughput screening. Primary patient cells can be grown on the CBC-1 with varying plating efficiencies. A linear correlation was observed between the number of cells seeded on the CBC-1 and the number of colonies formed. Two siRNA delivery methods were compared on the CBC-1 and higher transfection efficiency into primary patient cells using Accell siRNA as compared to lentiviral-vector mediated delivery was found. However, both siRNA delivery methods led to suppression of target gene expression. Also demonstrated was the effectiveness of different ESR1 siRNAs individually and as a pool for inhibiting MCF7 colony growth at different time points and in real-time. These studies validate the utility of the CBC-1 at identifying inhibitors of primary patient tumor cells that can grow in an anchorage-independent fashion. MCF7 cells are thought to be tumor-initiating cells and thus are envisioned as one cell type that may be targeted for therapy in accordance with the present invention. The data presented herein provide evidence of the CBCS translatability into a clinical setting for cancer target identification and personalized formulation of therapy.

While previously reported TCM siRNA screening methods have been used for the identification of genes essential for viability and proliferation of breast cancer cells, these assays utilize cell lines growing on flat surfaces. For these assays, attachment of the cells is essential for the incorporation of underlying siRNA. Thus, targets obtained from these studies were most often individually validated using anchorage-independent growth assays. In some instances, cells responded differently upon validation, which further emphasizes the need for siRNA screening of cells growing in an anchorage-independent, 3D fashion.

There have been previous attempts at developing high-throughput anchorage-independent growth assays. Some involved using 96-well plates, with decreased assay time from 21 to 28 days to 1 week, and cell numbers from 20,000 cells/dish to 1,000-2,000 cells/well (Ke, N. et al. Biotechniques 36, 826-828, 830, 832-823, 2004). The use of Alamar blue for colony readout also allowed for automated colony counting using the CytoFluor® Series 4000 Multi-Well Plate Reader. However, the need for a separate cell transfection step prior to plating cells in agar increased assay time and resulted in further cell loss. In addition, the use of Alamar blue for cell staining limits the ability to obtain a real-time chemosensitivity response, and does not allow for the identification of drugs that might lead to resistance. The 96-well format supports the testing of a larger number of inhibitors than previously possible, but is still unable to provide efficient real-time siRNA screening in 3D.

Other large-scale siRNA screens in 3D employed the pooled shRNA library drop-out approach (Westbrook, T. F. et al. Cell 121, 837-848, 2005; Kolfschoten, I. G. et al. Cell 121, 849-858, 2005). For these assays, primary cells are virally transduced with shRNA libraries and then cultured in 3D to identify inhibitors of cellular transformation. While these assays identified potential tumor suppressor genes, they could not be employed as an in vitro diagnostic test for identification of patient-specific therapies. For these assays, every cell has to be transduced with at least one viral replicon; cells that do not grow in these assays are correlated with shRNA lethality. Because the cells are transduced with shRNA prior to plating, this approach will not work for screening of inhibitors of primary patient cells, which do not grow at 100% plating efficiency. Cell death under these conditions could be attributed to either low plating efficiency or shRNA lethality. Because the approach presented herein employs a transfection method that occurs in cells growing in an anchorage-independent environment, lack of growth under these conditions is solely attributed to siRNA transfection. Therefore, it is essential to have on-agar transfection/transduction of siRNA/shRNA in order to perform functional genomic screens for inhibitors of anchorage-independent cell growth.

These studies demonstrate that the CBCS is a superior technology compared to other technologies for screening siRNA capable of inhibiting anchorage-independent, 3D primary patient tumor cell growth. These studies validate a first-generation CBCS which can be used for determination of plating efficiency of patient-specific cells, used as a siRNA transfection method for high siRNA incorporation, and used to optimize silencing efficiency of target genes as well as cytostatic efficiency. Demonstrated herein is the ability of the CBCS to grow patient tumor cells which incorporate underlying siRNA at high efficiency. Also demonstrated herein is the high specificity and efficiency of siRNA suppression of target genes and inhibition of tumor cell growth with the CBCS. Thus, the CBCS provides a powerful tool for functional genomic profiling of primary patient cells as well as for identification of targeted and efficacious patient-specific treatment modalities.

Example 2

Development and Use of CBCS Test Cancer BioChip for Cell-Specific Functional Genomic Profiling This investigation demonstrates the use of the CBCS as a powerful tool for functional genomic screening of inhibitors of anchorage-independent breast cancer cell growth. A first generation CBCS (CBC-1) was used to develop a biochip ("Test Cancer BioChip") containing siRNA for current drugable breast cancer gene targets to show its efficacy for the identification of clinically relevant breast cancer targets.

Materials and Methods
Cell Culture

MCF7 and SK-BR-3 cells were obtained from American Type Culture Collection (ATCC, Manassas, Va.). They were passaged once to generate a tree and cryopreserved until use. Following resuscitation, cells were passaged for less than six months. Authentication of cell lines was performed by ATCC using short tandem repeat profiling.

MCF7 cells were maintained in DMEM (Hyclone Laboratories, South Logan, Utah) supplemented with 10% Fetal Bovine Serum (FBS, Sigma Aldrich, St. Louis, Mo.) and 1% Antibiotic-Antimycotic (Invitrogen catalog number 15240-062, Carlsbad, Calif.). SK-BR-3 cells were maintained in RPMI (Sigma Aldrich) supplemented with 10% FBS and 1% Antibiotic-Antimycotic. At approximately 70 to 80% confluency, cells were either passaged using 0.05% Trypsin-EDTA (Hyclone Laboratories) or applied on the Test Cancer BioChip.

siRNA

Pools of four sequences of siRNA (Accell siRNA, Dharmacon Laboratories, LaFayette, Colo.) targeting each gene on the Test Cancer BioChip were prepared to give a final concentration of 10 μM on the CBC-1. These include proliferation genes (MKI67, AURKA, BIRC5, CCNB1, MYBL2), estrogen related genes (ESR1, PGR, BCL2, SCUBE2, ESR2), HER2 genes (ERBB2, GRB7), invasion genes (CTSL2, MMP11, CD68, BAG1, GSTM1), druggable gene targets (IGF1R, TNFRSF10A, TNFRSF10B, FNTB, BRAF, MAPK1, PIK3CA, CS K, HSPCA, HDAC1, DNMT1, DMAP1), and negative controls (ACTB, GAPDH, RPLP0, GUSB, TFRC, cyclophilin, non-targeting, no siRNA). We also included control siRNA for measurement of transfection efficiency (Accell Green). siRNA concentrations were measured using a Biotek Epoch Spectrophotometer (Winooski, Vt.).

Transfection Efficiency

The ability of breast cancer cells to incorporate Accell Green (Dharmacon), a fluorescent siRNA, on the CBC-1 was used to assess transfection efficiency. High transfection efficiency indicates that a large portion of the cells integrated the siRNA, which is essential for an effective siRNA screening assay. Accell Green, at a concentration of 10 μM, was tested, as well as a non-targeting control, which did not exhibit fluorescence. Five replicates were performed for each screen. A z-stack of images was taken of the same region of each well in both bright field and fluorescence using a 10× microscope objective. Images were acquired using a QICAM (QImaging®, Surrey, BC) mounted on an inverted Motic (Richmond, BC) AE31 microscope using QCapture Pro Imaging Software (QImaging®). Macros written in Image J (National Institutes of Health, Bethesda, Md.) were used for analysis. Cells were counted in each image, and those cells that exhibited fluorescence intensity greater than 2*SD over the non-targeting control mean were determined to have incorporated the Accell Green. Transfection efficiency for each cell line was expressed as a percentage of cells showing a fluorescent signal. Data are presented as mean transfection efficiency±SEM.

Cytotoxicity Screening on a Test Cancer BioChip

The Test Cancer BioChip was designed using the first-generation CBCS (CBC-1). It evaluated the cytostatic effects of the above-mentioned siRNAs in quintuplicate. The CBC-1 consisted of 50 well coverslips, allowing for the screening of 50 individual compounds, and thus screening of all siRNAs required use of four CBC-1 slides. Anchorage-independent growth was obtained by using soft agar as a base matrix to inhibit cellular attachment and as a top matrix for mixing with cells and immobilization on top of the different siRNAs. After application of cells (500-700 cells/well), the CBC-1 was incubated at 37° C. with 5% $CO_2$ for up to 15 days until distinct colonies could be observed using an inverted microscope. The CBC-1 was covered with cell-specific medium at day 1 after application of the cells and fed twice a week thereafter. Colony growth was quantified by imaging individual CBC-1 wells at a series of time points: 2, 7 or 8, and 14 or 15 days post seeding on the CBC-1 for MCF7 cells, and 2, 10, and 15 days post-seeding for the SK-BR-3 cells. In order to capture the 3D nature of cell growth, a series of images were taken along the z-axis for each well at each time point using a 4× microscope objective. After 14 or 15 days on the CBC-1, cells were stained for viability using MTT (Invitrogen) dissolved in PBS.

Data Analysis

Macros written in Image J were employed for image analysis. A z-stack of minimum intensities was created for each well at each time point. A mask was then produced using an appropriate threshold and used to obtain cell count and cell size distribution. A number of parameters were assessed in order to completely evaluate the effects of siRNA on cell growth. These include total cell count and change in cell count, which were measured to identify siRNA that completely killed cells, and change in average cell size that was calculated to determine siRNA causing retardation in growth. Change in average cell size was calculated between day 2 and each of the other time points and expressed as percent of controls on each CBC-1. Measured particles were considered to be colonies if they were larger than average cell size at day 2 plus two standard deviations. Relative change in colony number was calculated by subtracting the number of colonies between day 2 and later time points, normalizing that number to total cell counts at day 2, and expressing it as a percent of controls. The main reason for measuring the change in cell size and numbers between day 2 and later time points was to eliminate the effect of cell clumps or overlapping cells in each well at day 2. For MCF7 and SK-BR-3 cells, the colony count by day 14 or 15 was determined to be inaccurate due to colonies becoming so large that they began to merge or overlap and was therefore not used for further analysis.

Doubling time was calculated to determine siRNAs which affected growth rate while cells were growing exponentially, and growth curves were drawn to assess effects on growth rate over time. Doubling time, td, was calculated using the equation:

$$t_d = \frac{\ln(2)}{k}, \quad (1)$$

where k is a growth rate constant. This rate constant was calculated by solving an exponential growth equation:

$$x(t) = x_0 e^{kt} \quad (2),$$

where x is the total area covered by cells, $x_0$ is the initial area covered by cells (day 2), and t is the elapsed time. This equation was solved using day 7 or 8 data for MCF7 and day 10 for SK-BR-3 cells because by day 14 or 15 colonies began to merge and overlap, and thus the area covered by cells was no longer increasing exponentially. Doubling time was normalized to controls on each individual slide. In order to determine the screening capability of the CBCS and thus validate the assay, a screening window coefficient, Z', was calculated using the formula:

$$Z' = 1 - \frac{3SD_+ + 3SD_-}{R} \quad (3)$$

SD+ is the standard deviation of the positive controls, SD− is the standard deviation of the negative controls, and R is the dynamic range calculated as the absolute value of the difference between the means of the positive and negative controls. ESR1 siRNA was chosen as a positive control for the MCF7 screens, as it is known that suppressing ESR1 expression in MCF7 cells inhibits growth and colony formation, and ERBB2 was applied as a positive control for SK-BR-3 cells as it is known to suppress their growth. Non-targeting siRNA and no siRNA were used as negative controls. A screening window coefficient in the range 0≤Z'≤0.5 indicates good screening power of the assay.

Results

Plating and Transfection Efficiency of MCF7 and SK-BR-3 Cells on the Test Cancer BioChip Growth of two very well characterized breast cancer cell lines was tested: MCF7 and SK-BR-3. Both cell lines express most genes targeted on the Test Cancer BioChip at comparable levels, with the exception of ESR1, PGR, SCUBE2, CCNB1, and IGF1R being higher in MCF7 cells, and GRB7 and ERBB2 being elevated in SK-BR-3 (data not shown). Thus, this study determined whether silencing these genes would result in cell-line specific suppression of growth on the CBC-1.

First assessed was whether these cells would grow and form colonies on the CBC-1 (plating efficiency) and incorporate siRNA (silencing efficiency). Plating efficiency of 39%±1% for MCF7 cells and 25%±1% for SK-BR-3 cells was observed. Transfection efficiency, which can be determined by measuring Accell Green fluorescence intensity levels, was found to be 79%±4% for MCF7 cells and 83%±3% for SK-BR-3 cells. These results show that both cell lines can be grown on the CBC-1 and a high percentage of the cells incorporate the underlying siRNA.

Reproducibility and Screening Power of the Test Cancer BioChip Using MCF7 Cells

Figure 6:
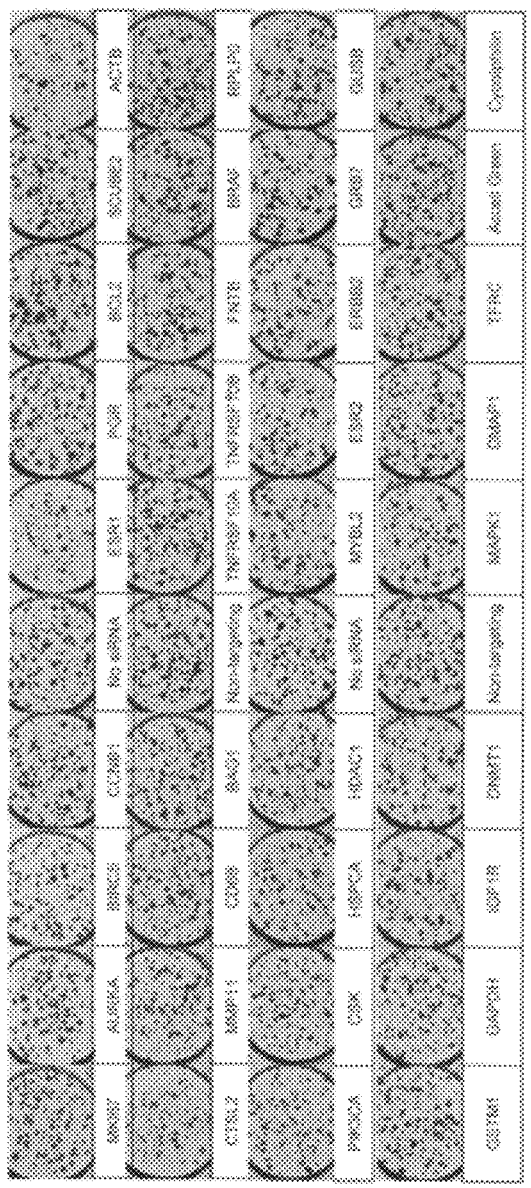
FIG. 6 provides representative images showing MCF7 colonies growing on the Test Cancer BioChip of the present invention in the presence of individual siRNAs. Cells were stained with MTT after 15 days on the CBC-1. Live colonies took up the dye and thus appeared dark and slightly larger due to the formation of formazan crystals.

The reproducibility of the Test Cancer BioChip was evaluated by performing two separate screens testing the effects of all targeted siRNAs on MCF7 growth. Images were obtained starting at day 2 and once a week thereafter to monitor colony growth in 3D. FIG. 6 shows representative merged z-stack images obtained at day 15 after culture of MCF7 cells on the CBC-1. These cells were stained with MTT for viability. Colonies appeared dark blue, but larger than their actual size, since the blue formazan crystals tended to deposit around the cells.

A number of parameters, including number of cells, average cell size, and the total area occupied by cells, were assessed to evaluate the effects of siRNA on cell growth on the CBC-1 at different time points. Percentage of cells forming colonies was also evaluated (plating efficiency), growth curves were plotted, and doubling time was calculated. A combination of these metrics was employed to quantify effects of each siRNA on cell growth and thus identify potential gene targets for therapy.

For the Test Cancer BioChip, the controls used included non-targeting, ACTB, GUSB, GAPDH, RPLP0, TFRC and cyclophilin siRNA as well as no siRNA. Using ANOVA followed by appropriate t-tests, it was determined that ACTB had a significant effect on MCF7 cell growth (FIG. 6), and thus could not be used as a control in this assay. Other siRNAs, including GAPDH and TFRC, produced minor effects.

Thus, these siRNAs were not used as controls in this study and all data were normalized to no siRNA and non-targeting siRNA on each CBC-1.

Figure 7:
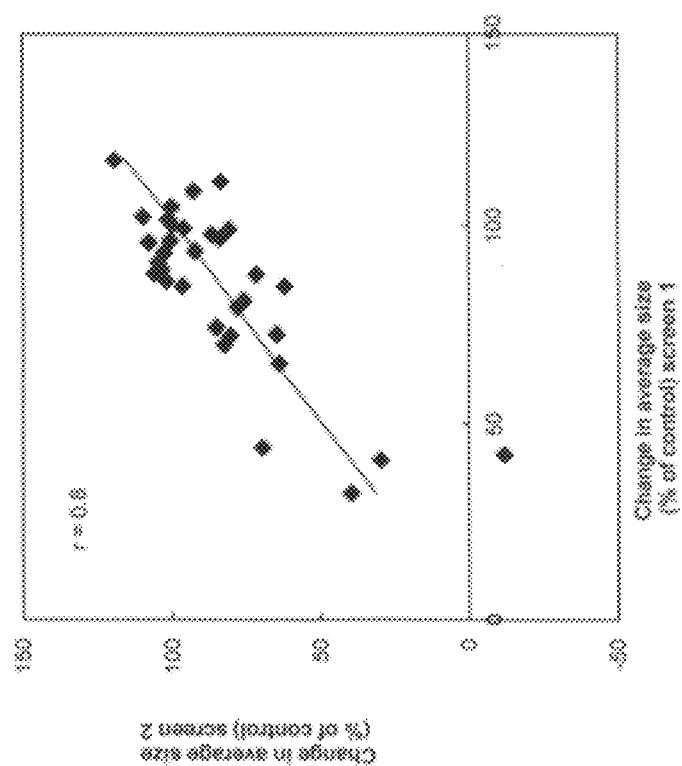
FIG. 7 is a scatter plot showing the correlation of percent change in average cell size from days 2 to 7 or 8 between two different CBC-1 screens used according to the embodiments of the present invention. The Pearson correlation coefficient between two screens=0.8, which indicates good reproducibility.

A Pearson correlation coefficient between the two MCF7 screens was calculated using each of the tested metrics including change in average cell size from day 2 to 7 or 8 (r=0.8, FIG. 7), and change in percent colonies from day 2 to 7 or 8 (r=0.8, data not shown). Overall, strong correlation was found between the screens.

The screening power of the CBC-1 using ESR1 siRNA as a positive control for the suppression of MCF7 cell growth was evaluated. It was found that ESR1 siRNA significantly suppressed MCF7 growth and colony formation on the CBC-1, reducing growth in average cell size to 36%±4% and 40%±4% of control from day 2 to 7 or 8 (FIG. 8A) and day 2 to 14 or 15 (data not shown), respectively. Reduction in number of MCF7 colonies formed between day 2 and 7 or 8, to 41%±4% of control (FIG. 8B) was observed. As shown in Table 3, there also was an increase in doubling time with ESR1 siRNA, to 265%±38% of control. The screening window coefficient, Z', was calculated for several screens using ESR1 siRNA as a positive control for MCF7 cells, and a Z'-factor of 0.3, indicating good screening power (0≤Z'≤0.5), could be obtained.

TABLE 3

Doubling Time of MCF7 and SK-BR-3 cells In Presence of different siRNAs on the CBC-1 (% of control).

| | Average doubling time (% of control) | |
|---|---|---|
| siRNA | MCF7 | SK-BR-3 |
| ESR1 | 265 ± 38 * | 142 ± 35 |
| ACTB | No fit | 236 ± 54 * |
| CTSL2 | 141 ± 12 * | 66 ± 6 ** |
| FNTB | 144 ± 8 * | 94 ± 11 |
| PIK3CA | No fit | 182 ± 34 * |
| CSK | 164 ± 29 * | 108 ± 13 |
| DMAP1 | 206 ± 47 * | 70 ± 6 |
| SCUBE2 | 101 ± 6 | 144 ± 18 * |
| ESR2 | 112 ± 7 | 150 ± 15 * |
| ERBB2 | 121 ± 20 | No fit |

* indicates siRNA causing a significant suppression (longer doubling time than control).
** indicates siRNA stimulating growth (significantly shorter doubling time than control).
In some cases the data did not fit the exponential growth model, showing almost complete suppression.
Only siRNAs that had the most significant effects in this study are shown.

Figure 8:
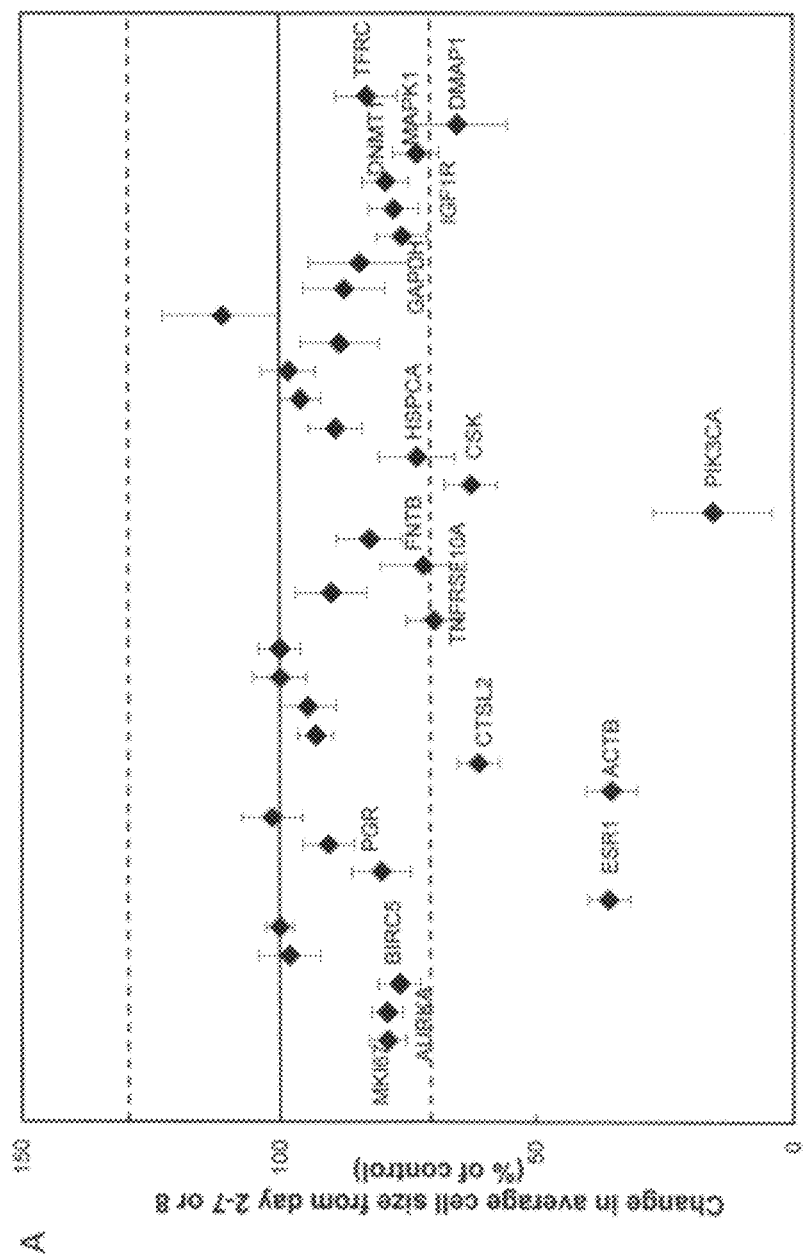
FIG. 8 shows inhibitors of MCF7 cell growth identified on the CBC-1. (A) shows change in average MCF7 cell size from days 2 to 7 or 8 normalized to control (n=6-11). (B) shows relative change in MCF7 colonies between days 2 to 7 or 8 normalized to control (n=6-11). Labeled siRNAs are significantly different from control in A and B (p<0.05). Dashed lines represent two standard deviations away from the control mean.
Figure 8:
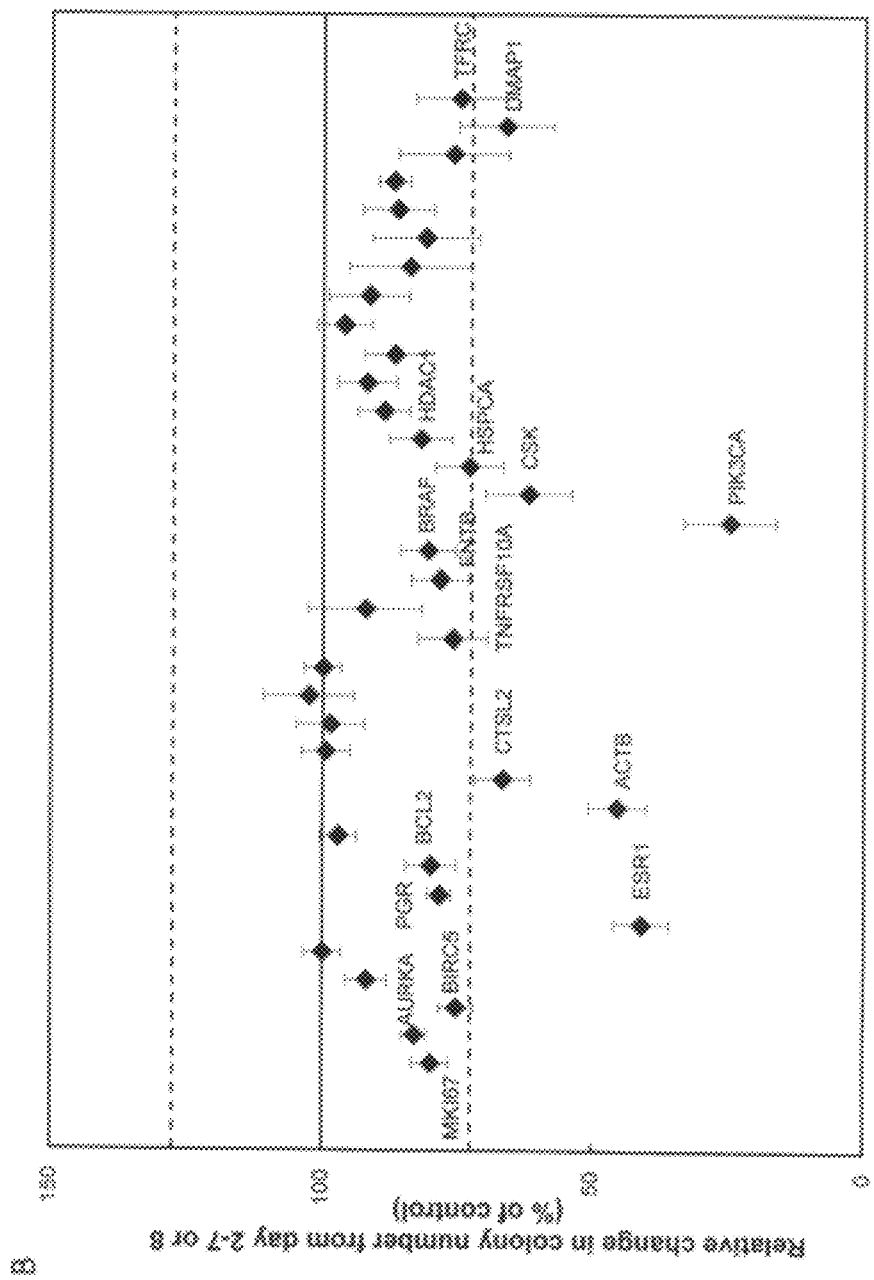
Figure 9:
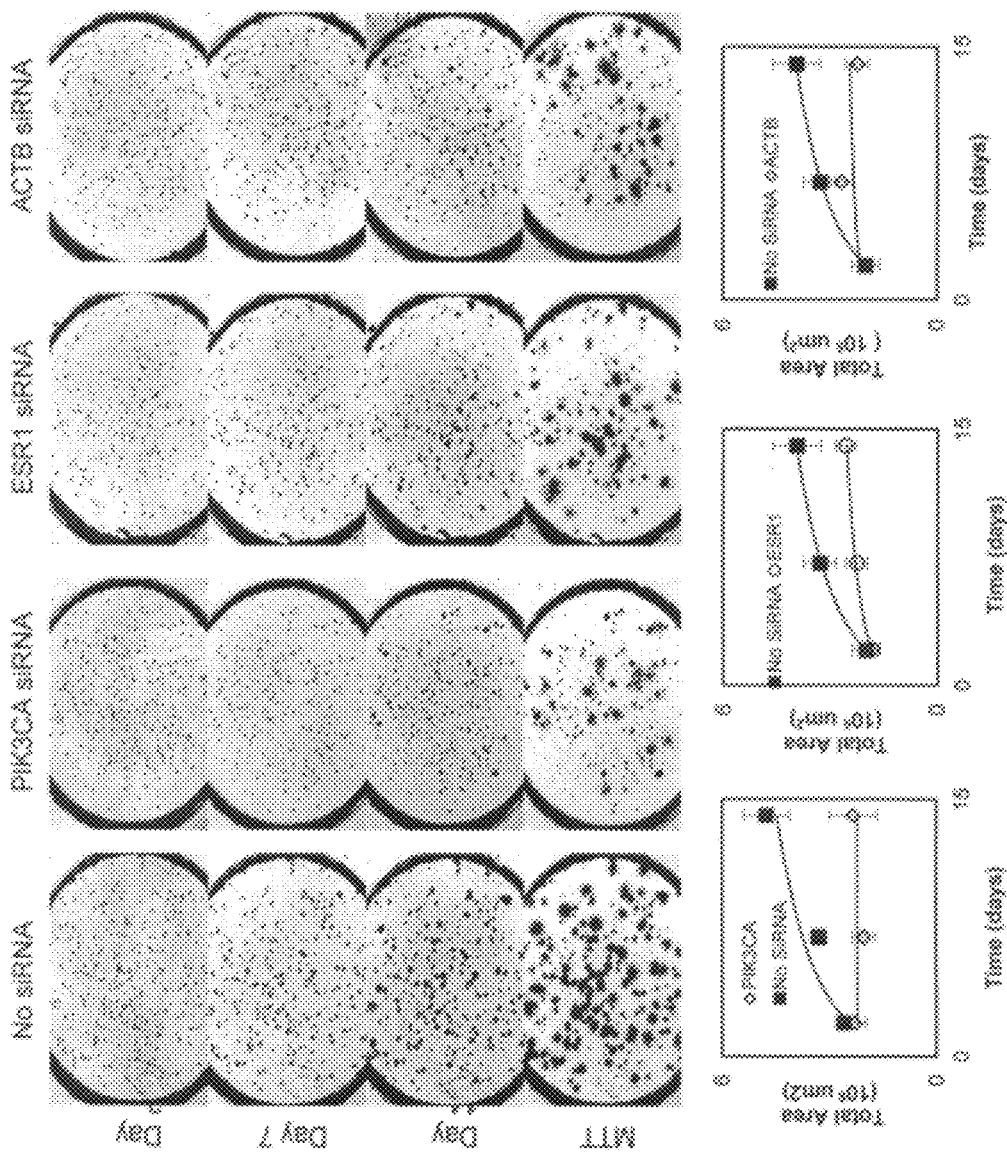
FIG. 9 provides (A) representative images showing the suppression of MCF7 colony formation over time in the presence of PIK3CA, ESR1, and ACTB siRNA. Live colonies stained in the MTT images (stained on day 14) appear dark and slightly larger due to the formation of formazan crystals. Each well is 3 mm in diameter; and (B) growth curves which show the change in total area vs. time for PIK3CA, ESR1, and ACTB siRNA and illustrate significant suppression caused by these siRNAs.

Identification of siRNA Capable of Inhibiting Anchorage-Independent Growth of the Luminal MCF7 Breast Cancer Cell Line on the Test Cancer Biochip After validating the assay using appropriate controls, the effect of the tested siRNAs on MCF7 colony formation was examined (FIG. 6). The change in average cell size (FIG. 8A) and relative change in colony number (FIG. 8B) were determined. Of the tested siRNAs, those targeting ESR1, PIK3CA, or ACTB caused the largest suppression in colony number and average size. Representative images and growth curves showing the suppression of growth over time caused by these siRNAs compared to that of controls are shown in FIGS. 9A and 9B. Colonies in the MTT-stained images appear larger than their actual size due to the deposition of formazan crystals around the cells. Growth curves (FIG. 9B) for MCF7 cells in presence of either ACTB or PIK3CA siRNA did not fit the exponential model. While ESR1 siRNA was shown to increase doubling time to more than 250% of control, doubling time for PIK3CA and ACTB siRNA could not be measured (see Table 3). These siRNAs almost completely suppressed growth to the point that the cells were no longer growing exponentially. These results show that ESR1, PIK3CA and ACTB siRNA significantly suppress anchorage-independent growth of MCF7 cells.

Other siRNAs caused smaller but statistically significant suppression of relative colony number and average size, with increase in doubling time. Those include CTSL2, CSK, and DMAP1 siRNAs, which suppressed colony size and number by more than two standard deviations from the control mean. Other siRNAs caused smaller, but statistically significant suppression in average size and relative colony number (FIG. 8), with small but statistically significant increase in doubling time (Table 3). These results show that the Test Cancer BioChip can identify siRNAs that inhibit anchorage-independent growth of MCF7 cells to different degrees.

Figure 10:
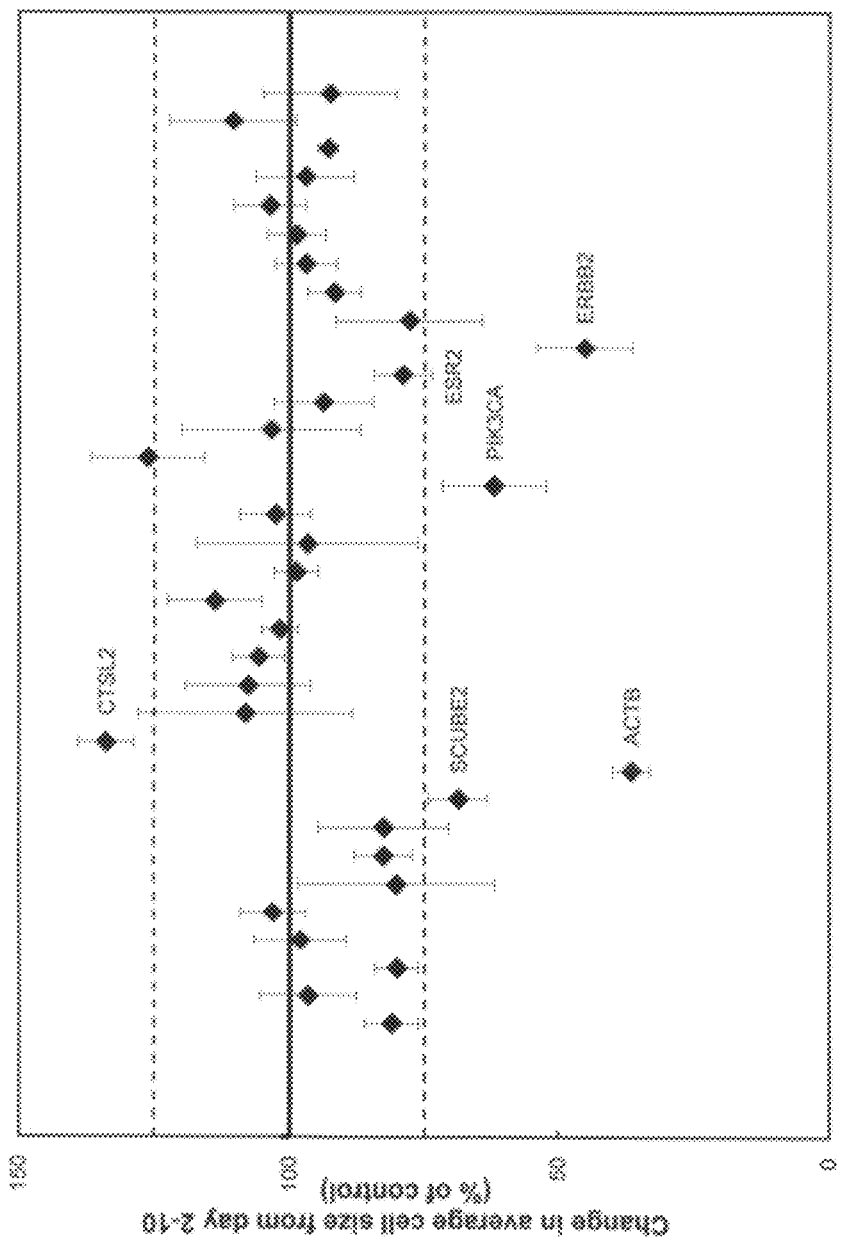
FIG. 10 shows inhibitors of SK-BR-3 cell growth identified on the CBC-1. (A) shows change in average SK-BR-3 cell size from days 2 to 10 normalized to control (n=3-5). (B) shows relative change in SK-BR-3 colonies between days 2 to 10 normalized to control (n=3-5). Labeled siRNAs are significantly different from control in A and B (p<0.05). Dashed lines represent two standard deviations away from the control mean.
Figure 10:
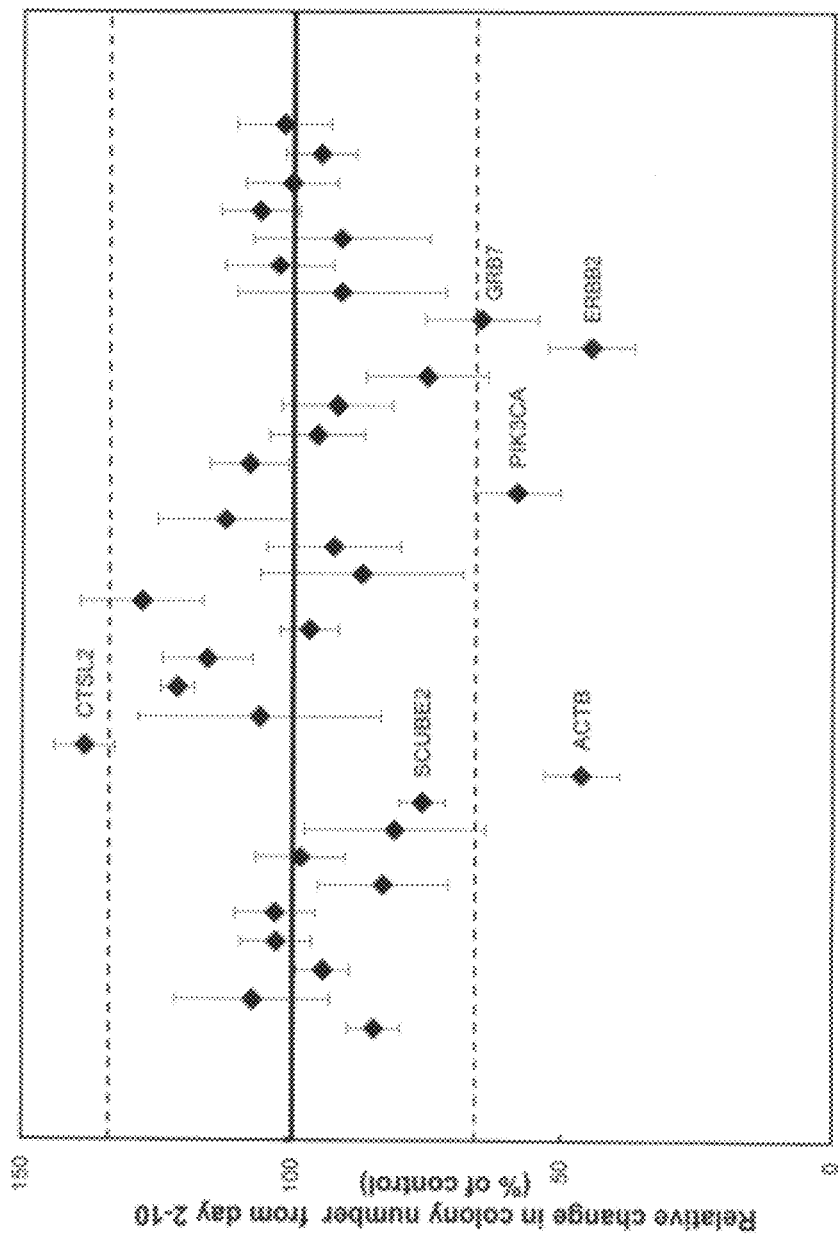

Identification of siRNA Capable of Inhibiting Anchorage-Independent Growth of the HER2 Positive SK-BR-3 Breast Cancer Cell Line on the Test Cancer Biochip The efficacy of these siRNAs to inhibit SK-BR-3 colony formation and growth on the Test Cancer BioChip as well as assessment of cell type-specific responses was determined. The positive control for these cells, ERBB2 siRNA, caused a decrease in SK-BR-3 colony number and size. It reduced average cell size change from days 2 to 10 to 45%±9% of control (FIG. 10A) and relative colony number change from days 2 to 10 to 45%±8% of control (FIG. 10B). While SK-BR-3 cells transfected with either no siRNA or non-targeting control grew exponentially on the CBC-1, SK-BR-3 cells transfected with ERBB2 siRNA did not. Therefore, doubling time could not be calculated for these cells (Table 3).

Comparison of the results from the Test Cancer BioChip using MCF7 and SK-BR-3 cells showed cell-specific effects of several siRNAs. While ERBB2 siRNA suppressed SK-BR-3 growth, it had no effect on MCF7 cells (FIG. 8, Table 3). In addition, growth of SK-BR-3 cells was not affected by ESR1 siRNA (FIG. 10, Table 3), showing a cell type-specific response.

Immediate effects of siRNA on SK-BR-3 growth on the Test Cancer Biochip were observed at day 2 for ERBB2, ESR2, CSK, CTSL2 and BRAF siRNAs. While ERBB2 and ESR2 siRNAs suppressed cell counts at day 2, CTSL2 siRNAs caused an increase (data not shown). These effects were maintained at later time points. At day 2, BRAF siRNA also caused an initial suppression and CSK siRNA caused an initial increase. These effects, however, were not maintained.

Figure 11:
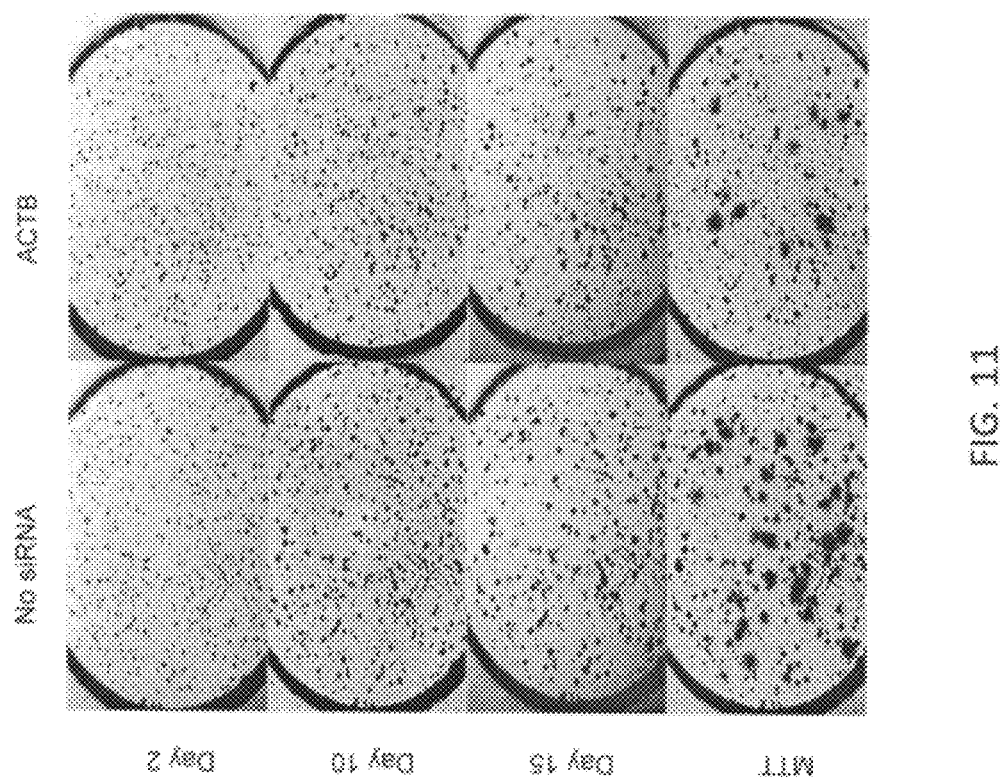
FIG. 11 provides representative images showing the suppression of SK-BR-3 cell growth over time caused by ACTB siRNA. Live colonies were stained with MTT on day 15.

At day 10, the strongest suppression of SK-BR-3 growth on the Test Cancer BioChip was observed using siRNAs for ACTB, PIK3CA and ERBB2 (FIGS. 10A and 10B). FIG. 11 shows representative images illustrating the suppression of colony formation over time caused by ACTB siRNA. The reduction in colony growth by this siRNA at day 10 was maintained at later time points. Other siRNAs, such as those targeting SCUBE2, ESR2 and GRB7 caused smaller but significant suppression in colony size and/or colony numbers, while CTSL2 siRNA caused a small but statistically significant increase in colony growth (FIGS. 10A and 10B). The siRNAs that inhibited colony formation also significantly increased SK-BR-3 doubling time (Table 3). The increased growth caused by CTSL2 siRNA was also evident from its significantly faster doubling time than control. While suppression of ACTB and PIK3CA inhibited growth of both SK-BR-3 and MCF7 cells, CTSL2 effects were opposite in the two cell lines.

In summary, the Test Cancer Biochip was employed as a fast, one-step tool for the identification of inhibitors of anchorage-independent breast cancer cell growth in real-time. Results from these studies showed cell type-specific effects of some siRNAs as well as effects that are unique to the 3D anchorage-independent nature of the CBCS assay.

Discussion

This investigation reports the development of a Test Cancer BioChip which contains siRNAs for breast cancer targets and controls in which the effects of the siRNAs were tested on anchorage-independent growth of a luminal breast cancer cell line (MCF7) and an HER2 positive cell line (SK-BR-3). When cultured on the CBC-1, both cell lines formed colonies, and a high percentage of cells incorporated the tested siRNA, indicating high transfection efficiency. Comparison of the percent of cells that formed colonies in the presence of all tested siRNAs revealed cell type-specific responses with several responses unique to this 3D assay.

Validation of Positive Controls on the Test Cancer BioChip

In this study, PIK3CA siRNA was identified to be a significant suppressor of anchorage-independent growth of both MCF7 and SK-BR-3 cells on the CBC-1. These results correlate well with findings from previous siRNA screens performed on these cells grown on flat surfaces. The importance of PIK3CA for the survival of MCF7 cells has been shown in a siRNA screen of the effects of a library of kinases on the growth of attached MCF7 cells on a flat surface (Iorns E. et al. PLoS One, 2009, 4:e5120). The agreement between the data presented herein and previously published data on the effects of PIK3CA on breast cancer cell lines further validates the efficacy of the CBC-1 for screening of targeted therapies for breast cancer.

Along with inhibitors common to both tested cell lines, the Test Cancer Biochip was found to be capable of identifying cell-specific effects of certain siRNAs. For example, significant inhibition of SK-BR-3 growth caused by ERBB2 siRNA was observed but no effect was observed on MCF7 cells. Inhibiting GRB7, another gene shown to be essential for the growth of ERBB2-positive cell lines including SK-BR-3, also caused significant suppression in colony number of these cells. MCF7 growth on the CBC-1, while not affected by inhibition of ERBB2, was significantly suppressed by ESR1 siRNA. These findings confirm the ability of the Test Cancer Biochip to detect cell-specific inhibitors of anchorage-independent growth. This also suggests that positive controls for CBCS screens need to be selected in a patient-specific manner.

Identification of Genes that Exhibit Anchorage-Independent Specific Effect on Breast Cancer Cell Growth A unique and surprising finding of the present investigation using the Test Cancer BioChip was the suppression of anchorage-independent growth of both tested cell lines by ACTB siRNA. This is the first investigation to report such a finding. In many assays, ACTB is used as a negative control since it is a major component of the cytoskeleton. Its suppression in most siRNA screens for cells growing on flat surfaces did not alter cellular phenotypes. However, ACTB has been reported to play a role in the migration, motility, and invasion of mammary epithelial cells including breast cancer cells (Yamaguchi H et al. Biochim Biophys Acta, 1773:642-52, 2007). In addition, siRNA targeting ACTB has been shown to reduce migration of MCF10A breast epithelial cells in a high throughput siRNA screen (Simpson K. J. et al. Nat Cell Biol, 10:1027-38, 2008) and to down-regulate AIB1, an adaptor protein involved in actin reorganization and polymerization, suppressed migration, invasion, proliferation and colony formation in MDA-MB-231 breast cancer cells (Wang, C. et al. Mol Cancer Res, 5:1031-9, 2007). While many chemotherapeutic agents currently act by disrupting the cytoskeleton, directly targeting ACTB with siRNA may have similar cytotoxic effects on the tumor cells. This finding stresses the utility of the 3D, anchorage-independent platform provided by the CBCS in identifying targets for breast cancer therapy.

Another unique and surprising finding of the present investigation was that inhibition of CTSL2, one of the tested invasion genes, suppressed MCF7 growth on the Test Cancer Biochip, but stimulated growth of SK-BR-3 cells. Cathepsins are lysosomal cysteine proteases involved in extracellular matrix degradation. Their intracellular activity is thought to play a role in cancer progression. Cell type-specific responses to silencing this gene have been observed. Two RNAi screens found that CTSL2 siRNA did not have any effect on MCF10A breast epithelial cells or human embryonic stem cells. Other studies have found that inhibition of cathepsin L significantly reduced tumor invasion and proliferation, increased cell death and prevented resistance to chemotherapy. While most studies were performed either on attached cells on flat surfaces or in mouse models, inhibition of cysteine proteases, including cathepsin L, has been shown in soft agar assays to significantly reduce colony formation and growth of ras-transformed NIH3T3 cells and MCF7 cells. The observed stimulation of SK-BR-3 growth on the CBC-1 with CTSL2 siRNA reported herein was surprising considering that inhibition of cathepsin L has been shown to reduce SK-BR-3 proliferation on flat surfaces. This effect may be mediated by the role of cathepsins in the cytosol, where they appear to play a role in initiating apoptosis. This may explain why inhibition of CTSL in tumor mouse models has been shown to be associated with increased intestinal and epidermal tumor progression, but with a decrease of pancreatic tumors. This suggests that the cell-specific effects of cathepsin L inhibition can only be observed in a setting that has high in vivo translatability. The 3D, anchorage-independent features of the CBCS allows for detection of this phenomenon when screening MCF7 and SK-BR-3 cells. The observation of such a cell type-specific response to CTSL2 siRNA points out the need for screening of individual patient cells to identify target therapies, one of the unique capabilities of the CBCS. In addition, the observation of effects on the Test Cancer BioChip, but not in other cell based assays, demonstrates the advantage of the more clinically translatable anchorage-independent growth platform provided by the CBCS.

Two other siRNAs caused large suppressions in MCF7 colony formation and growth (reduced colony size and relative colony number by more than two standard deviations of the mean). These include CSK and DMAP1 siRNAs. CSK siRNA, which targets c-Src, suppressed MCF7 growth, but not SK-BR-3 growth, on the CBC-1. It has been shown that silencing c-Src expression in MCF7 cells significantly reduces cell migration and proliferation. However, it also has been shown that high-throughput RNAi screens do not have an inhibitory effect of CSK siRNA on HCC1954, MCF10A or human mammary epithelial cells (HMECs). The present finding supports the likelihood of a cell type-specific response to this siRNA and again points out the need for testing individual patient cells. Targeting DMAP1 also caused significant inhibition of MCF7 growth on the CBC-1. DMAP1 is known to form a complex with DNMT1 and repress transcription in tumor cells. DNMT1 siRNA caused a smaller but statistically significant suppression of MCF7 growth on the CBC-1. Previous studies have shown that inhibiting DNMT1 hindered growth of MCF7 cells and HMECs. MCF7 suppression by DNMT siRNA previously was shown for both growth of attached cells and for cells grown in an anchorage-independent fashion.

Although the present investigation focused on siRNAs which caused the most gene suppression, as those genes would be the most likely candidates for therapeutic targets, more minor gene suppressors were identified using the Test Cancer BioChip. Inhibition of genes including AURKA, MKI67, BIRC5, FNTB, BRAF and IGF1R previously has been shown to suppress MCF7 cell growth. The present investigation demonstrated only mild suppression of anchorage-independent growth of MCF7 cells caused by these siRNAs. Other studies relying on growth of attached cells on flat surfaces found that inhibiting AURKA and FNTB suppressed SK-BR-3 growth. No response of SK-BR-3 cells to these siRNAs on the Test Cancer BioChip was found. These results point out that the effects of inhibiting certain genes may be dependent on cell growth on flat surfaces and/or cell-cell contact. These observations, therefore, further emphasize the importance of screening effects of compounds on anchorage-independent cell growth.

This investigation demonstrates that the CBCS is a powerful tool for determining cell type-specific responses to silencing of individual genes. We identified ACTB to be a novel suppressor of MCF7 and SK-BR-3 colony formation in a 3D anchorage-independent manner, while previous studies did not find effects of this siRNA on cells growing on flat surfaces. We also found a cell type-specific response to CTSL2 siRNA.

The results obtained stress the utility of the more clinically relevant 3D platform provided by the CBC-1 for identifying targets for breast cancer therapy as well as the need for patient specificity in choosing an effective therapy. The 3D, anchorage-independent platform provided by the CBCS, which more closely mimics cellular growth in vivo, allows for the identification of effects which have not been observed in assays conducted with attached cells on flat surfaces. Thus, the inhibitors identified with the CBCS may have improved clinical translatability. Moreover, the ability of the CBCS to quantify real-time colony formation and growth allows for the identification of siRNAs which cause immediate effects as well as those which cause downstream effects. Thus, the CBCS provides many unique features which facilitate the identification of gene targets for novel, individualized cancer therapy.

Example 3

Classification of Breast Cancer Tumors

Material and Methods

For these studies, sixteen invasive breast cancer tumors with corresponding normal adjacent tissue (NAT) from five patients, and one normal tissue from the other breast removed for prophylactic mastectomy, were obtained. Three of the patients were estrogen receptor (ER)-negative, progesterone receptor (PR)-negative, Her2-negative (N,N,N); two were ER-positive, PR-negative, Her2-negative (P,N,N); eight were ER-positive, PR-positive, Her2-negative (P,P,N), two were ER-positive, PR-negative, Her2-positive (P,N,P), and one was a sarcoma. The patients possessed different features that are summarized in Table 4. Ductal Carcinoma In Situ (DCIS) also was observed in 9 patients.

TABLE 4

Patient Pathology Report Summary

| | | # of Patients |
|---|---|---|
| Age Range: 28-84 years old | | |
| Ductal/Lobular | | |
| | Ductal | 6 |
| | Lobular | 3 |
| | Mixed | 2 |
| | Unknown | 5 |
| Stage | | |
| | pT1 | 2 |
| | pT2 | 5 |
| | pT3 | 6 |
| | Unknown | 3 |
| Node | | |
| | pN0 | 5 |
| | pN1 | 5 |
| | pN4 | 1 |
| | pNX | 1 |
| | Unknown | 4 |
| Metastasis | Present | 4 |
| Type | ER+ | 12 |
| | PR+ | 9 |
| | HER2+ | 2 |

Patient tumor samples were shipped in RPMI-1640 containing antibiotics, 10% Fetal Calf Serum and 2.5 µg/ml Fungizone and maintained cold during shipment. Upon arrival to the research facility, tissue was immediately processed for preparation of tumor cells. An aliquot from each tumor sample was frozen immediately and processed in conjunction with an aliquot obtained from the isolated tumor cells for gene expression analysis. Collagenase types 3 and 1 sequentially were used to digest the tissue and isolate cells. The cells were cultured in flasks coated with Geltrex (Invitrogen), an extracellular matrix that mimics conditions found in the mammary gland. HuMEC medium (Invitrogen) was used, which is designed for the culture of human mammary epithelial cells.

Results

To investigate the intrinsic molecular classes of the different tissue samples, gene expression profiling was performed on half of the tumor tissue using Affymetrix GeneAtlas U219 microarrays. For each tissue sample, the expression pattern of 49,386 different probe sets targeting the entire human genome were examined and 16,317 probe sets were found to be expressed at a level that is higher than background signal. These probe sets represented 9,149 genes. First, supervised hierarchical clustering was performed using BRB-Array Tools to classify the patient population according to their gene expression pattern. Using the "intrinsic gene subset" (Sorlie, T. et al. Proc Natl Acad Sci USA 100:8418-8423, 2003) which corresponds to 496 genes on the U219 microarrays, the patients were classified into five classes; luminal-A n=4, basal-like n=3, lobular n=2 tumor and 2 NAT, normal-like n=4 tumors and 1 NAT, and NAT n=3 (data not shown). There were not sufficient numbers of Her-2 positive patients to obtain a unique class for using this approach. In fact, both Her-2 positive patients clustered with the Luminal-A group since they also had high levels of ER. Interestingly, only 3 out of the 6 NAT tissue clustered together, with one being the tissue obtained from prophylactic mastectomy. The other 3 NAT had gene expression profiles that were indicative of microinvasion, with one patient having almost identical gene expression profiles for the tumor and the NAT. These observations emphasize the need to obtain normal tissue from areas that are not adjacent to tumor tissue.

Cells were successfully grown from all but 4 of the patients. From 3 of these 4 patients, a few viable cells were able to be isolated, but they did not divide in culture. Several factors could have affected the successful isolation of cells from these samples, including the fibrous nature of some of the tumors as well as the time elapsed following surgery where the tissue was allowed to dry before it was placed in medium.

Gene expression analysis was used to determine what types of cells were cultured from each patient tissue prior to application on the Test Cancer BioChip. The mammary gland is a complex organ containing several cell types that form ducts and lobules embedded in a stromal matrix. Several mammary cell types could grow in culture including: Endothelial, hematopoietic, stromal, and several distinct epithelial subsets of cells. Epithelial cells include hormone receptor positive (mature luminal (ML)), and hormone receptor negative (Mammary Stem Cell (MaSC)), Luminal Progenitor (LP), and Myoepithelial. CD49f, EpCAM, Keratin 8/18, Keratin 14 and other markers have been used to distinguish among these different types of mammary epithelial cells (Yeh, I T et al. Arch Pathol Lab Med 132:349-358, 2008).

Figure 12:
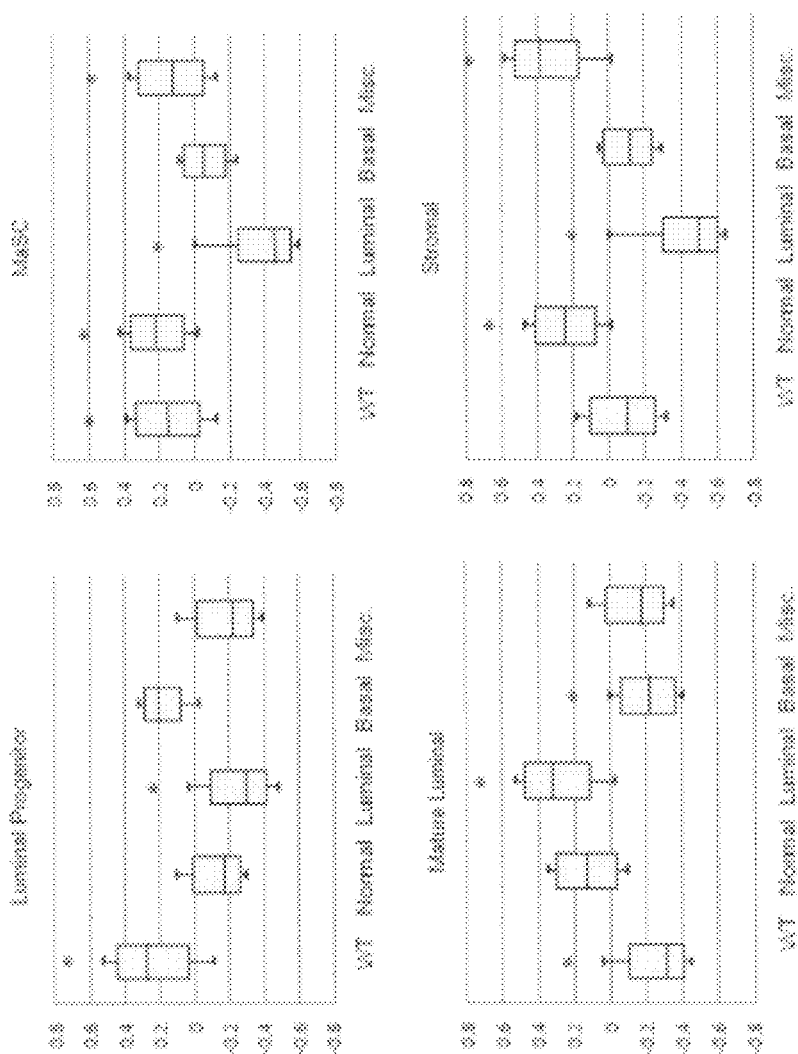
FIG. 12 shows results from GSEA analysis using ML, LP, MaSC or Stromal cell signatures on patient tissue samples according to the embodiments of the present invention.

Gene Set Enrichment Analysis was employed using published gene signatures for mammary epithelial and tumor-initiating cells (Creighton, C J et al. Proc Natl Acad Sci USA 106:13820-13825, 2009; Lim, E. et al. Nat Med 15:907-913, 2009) to determine which cell types are mostly present in the tissue and its corresponding cultured cells. FIG. 12 shows results from GSEA analysis using ML, LP, MaSC or Stromal cell signatures on patient tissue samples. The Luminal tumors were found to be enriched for ML markers, normal tissue (WT) and Normal-like (Normal) were enriched for LP and MaSC markers, and the Lobular tumors (Misc) were enriched for MaSC and Stromal cell markers. It is anticipated that early passage cells will be much more representative of the tissue with enrichment for MaSC, stromal, and tumor-initiating cells with further passage.

When gene signatures for each mammary cell type in tumor tissue were examined and compared to cells, only 5 tumor tissues with markers unique for the ML phenotype were found. Only one of those was hormone receptor positive in culture (P29). This sample was from an early passage, while the other samples were from later passages. While later passage cells did not express mature luminal markers, they expressed tumor-initiating, MaSC and stromal markers without any hormone receptor expression. The other patient tissues expressed mostly LP and MaSC markers and were cultured on Geltrex in the presence of HuMEC. Cells obtained from these patients maintained the LP and MaSC phenotype, but became only MaSC with further passages (data not shown). These observations show that tumor-initiating cells can be cultured from patient tissue and these cells can be targeted on the CBC-1 for cancer drug discovery.

Identification of Patient-Specific Effects of siRNAs Using the Test Cancer BioChip After successfully validating the utility of the Test Cancer BioChip using well characterized cell lines and positive controls, this assay was used to evaluate the effects of the 35 selected siRNAs on the above-mentioned primary cells that were obtained from breast cancer patients.

The strongest response to hormone receptor suppression by siRNA was observed in the patient with a Mature Luminal gene expression signature. In this patient, immediate suppression of cell numbers and colony formation by PGR siRNA with a slightly milder response to ESR1 siRNA was obtained (data not shown). Thus, the CBC-1 can identify patients that would respond to hormone therapy.

Figure 13:
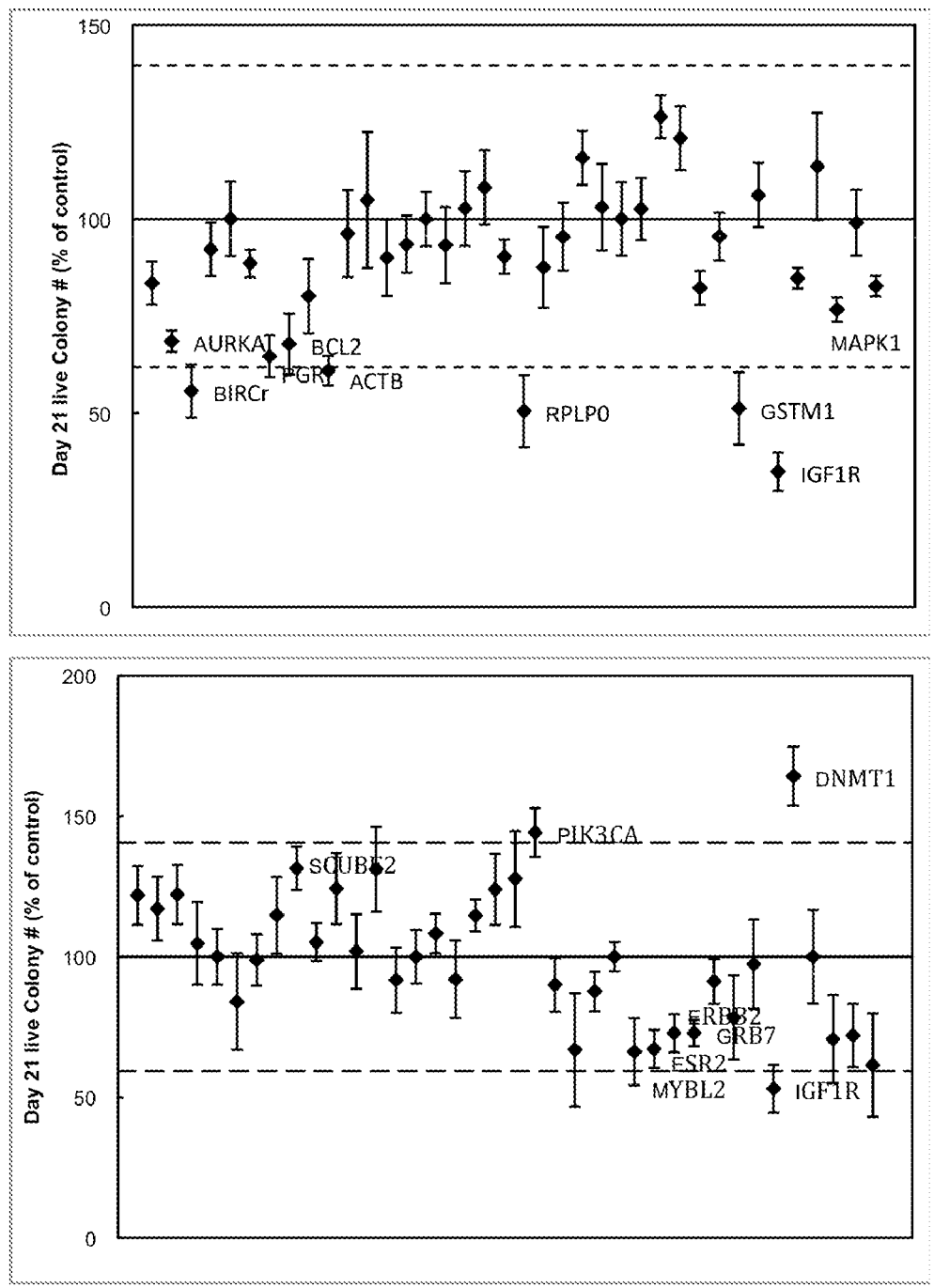
FIG. 13 shows percent colonies formed from two luminal-A patients, with one patient showing no response to PIK3CA siRNA (top) and the other patient showing an increase in colony formation (bottom).

PIK3CA siRNA was also found to have significant effects on several patient cells in addition to the MCF-7 and SK-BR-3 cells. PIK3CA siRNA significantly suppressed colony formation and growth in some patients. However, in other patients, it was found that it caused the opposite effect, i.e., a significant increase in colony growth. The response to PIK3CA siRNA was independent of the intrinsic molecular subtypes. FIG. 13 shows percent colonies formed from two luminal-A patients, with one patient showing no response to PIK3CA siRNA and the other showing an increase in colony formation. These results show that ER/PR/Her2 status is not sufficient to predict the response to siRNA and thus genes necessary for tumor growth. Another significant conclusion is that a therapy targeting a certain gene, such as PIK3CA, may be very effective in inhibiting tumor growth in some patients but actually stimulate growth of the tumor in others. Therefore, the present studies demonstrate that personalization of therapy is essential for effective treatment of breast cancer.

Another potential gene target for therapy that was identified to be effective for certain patients is IGF1R. IGF1R siRNA significantly inhibited colony formation and growth in two luminal-A patients, shown in FIG. 13 (top and bottom). Other tested patients, however, showed no response to IGF1R siRNA. While ACTB siRNA inhibited colony growth of both MCF-7 and SK-BR-3 cells, it inhibited colony formation in only one of the tested patient cells (FIG. 13, top).

Discussion

These studies show that the CBC-1 was able to successfully determine genes essential for growth of patient tumor cells and thus identify targets for potential therapy. Comparison of gene expression profiles between the different tumor classes using the CBC-1 allows for the identification of differentially expressed genes that then can be tested on a higher-throughput CBCS. Furthermore, dysregulated signaling pathways can be identified using the GenMapp software to compare expression in the cells relative to normal cells. These studies allow for the identification of the key genes that should be targeted with siRNA on the Cancer BioChip with siRNA.

For every breast cancer patient, the clinical pathology report with gene expression profiles can be matched, allowing for gene expression-based classification of the tumors. Currently, a small number of markers are employed in the clinic for classification and diagnosis of breast cancer patients. The approach presented herein allows for the examination of all the markers for each type of breast cancer in one test. First, the levels of Keratins, E-Cadherins, p63, ER, PR, and Her-2 will be individually evaluated, followed by GSEA analysis, to examine the molecular signature of each cell type in the mammary gland. This will allow for the comparison of each patient tumor to others, and for the identification of key signaling pathways that need to be targeted on the Cancer BioChip. Examination of gene expression profiles from the cells will further narrow down the number of abnormally expressed tumor genes that need to be tested on the CBCS for each patient.

Testing of these cells on the CBCS reveals the complexity of each molecular class, and allows for the functional genomic profiling of each patient. For some patients, targeting one gene at a time may not be sufficient to block colony formation. For these patients, follow-up assays may be necessary, testing with different combinations of partially effective siRNAs. The results can be mapped using GenMAPP to show which signaling pathways are most effective at suppressing tumor growth when targeted with siRNA.

It is envisioned that with the use of the CBCS, breast cancer patients will be classified based on their response to siRNA targeting particular signaling cascades. For example, functional genomics classes would be ER, PR, erbb2, PI3kinase and other gene responsive tumors.

In summary, the CBCS is able to identify siRNAs capable of inhibiting tumor-initiating cell growth, and provides a novel way of classifying breast cancer patients. Results from these studies reveal functional genomic profiles of breast cancer that can predict in vivo response.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for individualized cancer patient therapy, comprising:
   obtaining tumor cells from a patient;
   detecting and identifying specific genes and/or gene products in the tumor cells to classify the type of cancer in the patient by:
   applying the tumor cells to a biochip comprising a first matrix, a second matrix and a plurality of active agents, said plurality of active agents targeting the specific genes and/or gene products, said specific genes and/or gene products consisting of proliferation genes MK167, AURKA, BIRC5, CCNB1 and MYBL2; estrogen-related genes ESR1, PGR, BCL2, SCUBE2 and ESR2; HER2 genes ERBB2 and GRB7; invasion genes CTSL2, MMP11, CD68, BAG1 and GSTM1; druggable gene targets IGF1R, TNFRSF10A, TNFRSF10B, FNTB, BRAF, MAPK1, PIK3CA, CSK, HSPCA, HDAC1, DNMT1 and DMAP1; and control genes ACTB, GAPDH, RPLP0, GUSB, TFRC and cyclophilin;
   growing the tumor cells in a three-dimensional, anchorage-independent fashion;
   measuring the three-dimensional growth of the tumor cells;
   detecting cancer cell type-specific responses of the patient by determining and identifying which one or more of the plurality of active agents affects the growth of the tumor cells of the patient; and
   formulating individualized cancer therapy for the patient based on the detection and identification of the one or more of the plurality of active agents, and administering said therapy to the patient.

2. The method according to claim 1, wherein the plurality of active agents comprise DNA, RNA, siRNA, shRNA, antibodies, small molecules, proteins, peptides, peptidomimetics, pharmaceutical compositions, drugs and combinations thereof.

3. The method according to claim 2, wherein the plurality of active agents comprise siRNA.

4. The method according to claim 1, wherein the first and/or the second matrix comprise at least one transfection agent embedded therein, said at least one transfection agent comprising chemical transfection agents, lipid based transfection agents, cationic lipid transfection agents, non-lipid based transfection agents, electroporation, molecular-based transfections, laser mediated transfection, pinocytosis transfection, osmotic lysis transfection, microinjection, viral delivery systems and combinations thereof.

5. The method according to claim 1, wherein the tumor cells further comprise a detectable label comprising selectable markers, fluorescent markers, fluorescent nanocrystals, quantum dots, fluorescent proteins, bacterial enzymes, and combinations thereof.

6. The method according to claim 1, wherein the first matrix and the second matrix are comprised of soft agar, agarose, hydrogels, methylcellulose alginate hydrogel, polyvinyl alcohol-hydrogel, collagen vitrigel, poly(2-hydroxylmethacrylate)hydrogels, PVP/PEO hydrogels, copolymers of 2-methacryloyloxyethyl, phosphorylcholine and combinations thereof.

7. The method according to claim 1, further comprising a means for observing the tumor cells comprising microscopy, scanning, laser scanning, fluorescence detection, automated fluorescence detection, a CCD camera, cell counter, automated colony counter, the human eye, FACS and combinations thereof.

8. The method according to claim 1, wherein the biochip is a calibration chip further comprising positive and negative control agents which optimize cancer cell culture modalities, specificity of active agents, transfection methods and reproducibility of the assay.

9. A cancer biochip diagnostic system for individualized cancer patient therapy, comprising a cancer biochip comprising a first matrix, and a second matrix, said first matrix having embedded therein a plurality of active agents which target specific genes and/or gene products consisting of proliferation genes MK167, AURKA, BIRC5, CCNB1 and MYBL2; estrogen-related genes ESR1, PGR, BCL2, SCUBE2 and ESR2; HER2 genes ERBB2 and GRB7; invasion genes CTSL2, MMP11, CD68, BAG1 and GSTM1; druggable gene targets IGF1R, TNFRSF10A, TNFRSF10B, FNTB, BRAF, MAPK1, PIK3CA, CSK, HSPCA, HDAC1, DNMT1 and DMAP1; and control genes ACTB, GAPDH, RPLP0, GUSB, TFRC and cyclophilin, wherein at least one specific gene of said specific genes and/or at least one gene product of said gene products are contained in tumor cells of a cancer patient which have been obtained from the cancer patient and applied to the biochip, wherein the first matrix and the second matrix allow the tumor cells to grow in a three-dimensional, anchorage-independent fashion, wherein the three-dimensional growth of the tumor cells is measured on the biochip to determine and identify which one or more of the plurality of active agents affects the growth of the tumor cells of the patient in order to formulate an individualized cancer therapy for the patient.

10. The cancer biochip system of claim 9, wherein the plurality of active agents comprise DNA, RNA, siRNA, shRNA, antibodies, small molecules, proteins, peptides, peptidomimetics, pharmaceutical compositions, drugs and combinations thereof.

11. The cancer biochip system of claim 10, wherein the plurality of active agents comprise siRNA.

12. The cancer biochip system of claim 9, wherein the first matrix and/or the second matrix comprise at least one transfection agent embedded therein, said at least one transfection agent comprising chemical transfection agents, lipid based transfection agents, cationic lipid transfection agents, non-lipid based transfection agents, electroporation, molecular-based transfections, laser mediated transfection, pinocytosis transfection, osmotic lysis transfection, microinjection, viral delivery systems and combinations thereof.

13. The cancer biochip system of claim 9, wherein the tumor cells further comprise a detectable label comprising selectable markers, fluorescent markers, fluorescent nanocrystals, quantum dots, fluorescent proteins, bacterial enzymes, and combinations thereof.

14. The cancer biochip system of claim 9, wherein the first matrix and the second matrix are comprised of soft agar, agarose, hydrogels, methylcellulose alginate hydrogel, polyvinyl alcohol-hydrogel, collagen vitrigel, poly(2-hydroxylmethacrylate)hydrogels, PVP/PEO hydrogels, copolymers of 2-methacryloyloxyethyl phosphorylcholine and combinations thereof.

15. The cancer biochip system of claim 9, further comprising a means for observing the tumor cells comprising microscopy, scanning, laser scanning, fluorescence detection, automated fluorescence detection, a CCD camera, cell counter, automated colony counter, the human eye, FACS and combinations thereof.

16. The cancer biochip system of claim 9, wherein the biochip is a calibration chip further comprising positive and negative control agents which optimize cancer cell culture modalities, specificity of active agents, transfection methods and reproducibility of the assay.

17. A method for affecting the growth of cancer cells, comprising exposing cancer cells to one or more active agents that target specific genes and/or gene products, said specific genes and/or gene products consisting of proliferation genes MK167, AURKA, BIRC5, CCNB1 and MYBL2; estrogen-related genes ESR1, PGR, BCL2, SCUBE2 and ESR2; HER2 genes ERBB2 and GRB7; invasion genes CTSL2, MMP11, CD68, BAG1 and GSTM1; druggable gene targets IGF1R, TNFRSF10A, TNFRSF10B, FNTB, BRAF, MAPK1, PIK3CA, CSK, HSPCA, HDAC1, DNMT1 and DMAP1; and control genes ACTB, GAPDH, RPLP0, GUSB, TFRC and cyclophilin.

18. The method according to claim 3, wherein the one or more active agents are identified by determining which one or more siRNA inhibit growth of the cancer cells, said siRNA comprising MK167 siRNA, AURKA siRNA, BIRC5 siRNA, CCNB1 siRNA MYBL2 siRNA, ESR1 siRNA, PGR siRNA, BCL2 siRNA, SCUBE2 siRNA, ESR2 siRNA, ERBB2 siRNA, GRB7 siRNA, CTSL2 siRNA, MMP11 siRNA, CD68 siRNA, BAG1 siRNA, GSTM1 siRNA, IGF1R siRNA, TNFRSF10A siRNA, TNFRSF10B siRNA, FNTB siRNA, BRAF siRNA, MAPK1siRNA, PIK3CA siRNA, CSK siRNA, HSPCA siRNA, HDAC1 siRNA, DNMT1 siRNA, DMAP1 siRNA, ACTB siRNA, GAPDH siRNA, RPLP0 siRNA, GUSB siRNA and TFRC siRNA.

19. The method according to claim 17, wherein the one or more active agents comprise DNA, RNA, siRNA, shRNA, antibodies, small molecules, proteins, peptides, peptidomimetics, pharmaceutical compositions, drugs and combinations thereof.

20. The method according to claim 17, wherein the method is efficacious for affecting the growth of cancer cells comprising breast cancer cells and ovarian cancer cells.

21. A method for treating cancer cells of a patient by inhibiting the growth of the cancer cells, comprising administering one or more active agents to the cancer cells that target specific genes and/or gene products of the patient, said specific genes and/or gene products consisting of proliferation genes MK167, AURKA, BIRC5, CCNB1 and MYBL2; estrogen-related genes ESR1, PGR, BCL2, SCUBE2 and ESR2; HER2 genes ERBB2 and GRB7; invasion genes CTSL2, MMP11, CD68, BAG1 and GSTM1; druggable gene targets IGF1R, TNFRSF10A, TNFRSF10B, FNTB, BRAF, MAPK1, PIK3CA, CSK, HSPCA, HDAC1, DNMT1 and DMAP1; and control genes ACTB, GAPDH, RPLP0, GUSB, TFRC and cyclophilin.

22. The method according to claim 21, wherein the one or more active agents comprises DNA, RNA, siRNA, shRNA, antibodies, small molecules, proteins, peptides, peptidomimetics, pharmaceutical compositions, drugs and combinations thereof.

* * * * *